US012734075B2

(12) United States Patent
Lenser et al.

(10) Patent No.: US 12,734,075 B2
(45) Date of Patent: Sep. 15, 2026

(54) SPLIT FORMATION OF UNITARY SUBSTRATES

(71) Applicant: The Procter & Gamble Company, Cincinnati, OH (US)

(72) Inventors: Todd Douglas Lenser, Liberty Township, OH (US); Randall Allen Myers, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 320 days.

(21) Appl. No.: 18/539,402

(22) Filed: Dec. 14, 2023

(65) Prior Publication Data

US 2024/0216183 A1 Jul. 4, 2024

Related U.S. Application Data

(60) Provisional application No. 63/478,400, filed on Jan. 4, 2023.

(51) Int. Cl.
*A61F 13/15* (2006.01)
*A61F 13/62* (2006.01)

(52) U.S. Cl.
CPC ...... *A61F 13/15739* (2013.01); *A61F 13/625* (2013.01); *A61F 2013/15878* (2013.01); *A61F 2013/15934* (2013.01)

(58) Field of Classification Search
CPC .............. A61F 13/15739; A61F 13/625; A61F 13/15699; B29C 65/087; B29C 66/0242
See application file for complete search history.

(56) References Cited

U.S. PATENT DOCUMENTS 5,059,277 A * 10/1991 Willhite, Jr. .......... B29C 66/433 156/580.1
6,773,527 B2 8/2004 Campbell et al.
8,745,827 B2 6/2014 Rocha
8,784,772 B2 7/2014 Berman
9,265,673 B2 2/2016 Stabelfeldt et al.
9,265,674 B2 2/2016 Hancock-cooke et al.
9,282,790 B2 3/2016 Rocha et al.
9,795,194 B2 10/2017 Rocha
10,076,162 B2 9/2018 Rocha
10,105,787 B2 * 10/2018 Wang .................. B29C 66/8322
10,159,313 B2 12/2018 Rocha et al.
(Continued)

FOREIGN PATENT DOCUMENTS

WO 2018006946 A1 1/2018

OTHER PUBLICATIONS

Unpublished U.S. Appl. No. 18/495,137, filed Oct. 26, 2023, to Todd Douglas Lenser et. al.
(Continued)

*Primary Examiner* — Daniel Mcnally
(74) *Attorney, Agent, or Firm* — Gregory P. Habiak; Christian M. Best

(57) ABSTRACT

Methods of forming a laminate may include conveying a first substrate through a first nip, where a first source of vibration energy may be used to alter a portion of the first substrate in the first nip to create an altered area. The method may include conveying the first substrate with the altered area and a second substrate into a second nip and using a second source of vibration energy to join the first substrate to the second substrate in the second nip.

20 Claims, 35 Drawing Sheets

(56) References Cited

U.S. PATENT DOCUMENTS

| | | | |
|---|---|---|---|
| 10,405,614 | B2 | 9/2019 | Rocha |
| 10,798,997 | B2 | 10/2020 | Rocha |
| 10,953,592 | B2 | 3/2021 | Rocha |
| 10,981,321 | B2 | 4/2021 | Rocha |
| 11,058,186 | B2 | 7/2021 | Rocha |
| 11,331,222 | B2 * | 5/2022 | Sakai ................ A61F 13/49012 |
| 2014/0349062 | A1 | 11/2014 | Chandrasekaran et al. |
| 2019/0224054 | A1 | 7/2019 | Silfverstrand et al. |
| 2019/0387846 | A1 | 12/2019 | Rocha |
| 2020/0179184 | A1 | 6/2020 | Kaiser |
| 2021/0045931 | A1 | 2/2021 | Linot |
| 2021/0162675 | A1 * | 6/2021 | Lehmann ............ B29C 66/7392 |
| 2023/0330621 | A1 | 10/2023 | Lenser et al. |
| 2023/0330630 | A1 | 10/2023 | Lenser et al. |
| 2023/0405943 | A1 | 12/2023 | Lenser |
| 2024/0060905 | A1 | 2/2024 | Lenser et al. |
| 2024/0140048 | A1 | 5/2024 | Lenser |

OTHER PUBLICATIONS

EPO Search Report and Opinion for 23216755.1 dated May 17, 2024, 6 pages.

EPO Search Report and Opinion for 25225619.3 dated Feb. 9, 2026, 07 pages.

* cited by examiner

600
$W_{200}$
300
400
45
500
200
102
MD
CD
500
45
101
402
406
100
$W_{102}$
406
$W_{101}$

600
$W_{200}$
300
400
200
500
45
MD
CD
402
406
100
$W_{100}$ $W_{200}$
600
300
400
45
200
500
MD
CD
402
406
100, 103
$W_{100}$ $W_{200}$
600
300
400
200
500
45
MD
CD
402
406
100, 103
$W_{100}$ 600
46
300
400
45
$W_{200}$
MD
CD
102
200, 203
402
406
500
101
100, 103
$W_{102}$
$W_{101}$

600
$W_{200}$
46
300
400
45
MD
CD
200, 203
402
406
500
100, 103
$W_{100}$ 300
200
302
103
104
106
110, 304

SPLIT FORMATION OF UNITARY SUBSTRATES

CROSS REFERENCE TO RELATED APPLICATION

This application claims the benefit of U.S. Provisional Application No. 63/478,400, filed Jan. 4, 2023, the entire disclosure of which is hereby incorporated herein by reference.

FIELD

The present disclosure relates generally to unitary formation of protrusions on substrates and more specifically to unitary formation of protrusions on substrates in which protrusion formation is performed independently of attachment to a second substrate.

BACKGROUND

The discussion of shortcomings and needs existing in the field prior to the present disclosure is in no way an admission that such shortcomings and needs were recognized by those skilled in the art prior to the present disclosure.

Unitary formation of protrusions in a substrate provides a high quality, aesthetically pleasing, low cost method of providing novel product features for disposable absorbent articles. Rotary formation may be implemented via a mold roll and an ultrasonic tool, such as a sonotrode, as disclosed in U.S. Pat. No. 8,784,772. Rotary formation may be used to form mechanical fasteners, protrusions, or hooks in a web. Rotary formation may form intermittent patches of hooks in a diaper, pant, and/or feminine absorbent article. The hook patches may comprise a primary or secondary fastener, a disposal tape, a portion of a refastenable side seam, an insert holding feature, or other refastenable elements.

Rotary formation may be implemented on an absorbent article converting line or may be implemented off-line from an absorbent article converting line. Rotary formation may be implemented at a first machine on a substrate, and then the substrate may be transferred to a second machine for application to an absorbent article. Rotary formation may utilize blade sonotrodes, rotary sonotrodes, or a plurality of sonotrodes. Rotary formation may use film, nonwoven, or laminate substrates. Substrates and/or protrusion regions may be continuous or intermittent.

Quality, speed, and robustness of hook formation may continue to be a challenge. Hook cavities may only partially fill. Hooks may fracture from the substrate after formation. Hooks may have low peak engagement forces with a mating substrate. Preferred product embodiments may not be realizable given process constraints in the related art.

A need therefore, exists for a method and/or apparatus to provide quality, speed, and robustness of hook formation.

SUMMARY

Various embodiments solve the above-mentioned problems and provide methods and devices useful for providing quality, speed, and robustness of hook formation.

Previous attempts to provide a high basis weight region, such as a film adjacent a nonwoven substrate to increase basis weight, surprisingly failed to provide benefits in quality and line rate. The thick film would not bond well with the nonwoven layer. The thick film rarely tracked straight, and mistracked in and out of the bond site. The substrates were also prone to wrinkling. A film substrate, or a laminate containing a film layer, may be preferred for rotary hook formation. Nonwoven substrates may have localized basis weight variation, with low and high basis weight regions and hooks may fail to form in localized low basis weight regions and the low basis weight regions may even experience burn-thru. A solution to rate limitations of hook formation has been discovered by which the hook formation is separated from the hook attachment to a second or larger substrate. Various configurations provided enable the first substrate to be optimized for line speed and product quality and may eliminate the need to bond adjacent nonwoven fibers.

Various configurations relate to a method of forming a laminate. The method may comprise providing a first device comprising an outer surface, providing a second device comprising a first source of vibration energy, and forming a first nip between the first source of vibration energy and the outer surface. A first substrate may be conveyed through the first nip, where the first source of vibration energy may be used to alter a portion of the first substrate in the first nip to create an altered area. The method may further comprise providing a third device comprising a second source of vibration energy and forming a second nip between the second source of vibration energy and the outer surface. The second nip may be downstream of the first nip. The first substrate with the altered area and a second substrate may be conveyed into the second nip and the second source of vibration energy may be used to join the first substrate to the second substrate in the second nip. According to various configurations, the first substrate may have a first cross-directional width, the second substrate may have a second cross-directional width, and the second cross-directional width may be larger than the first cross-directional width. The first substrate may also comprise a plurality of strips.

The disclosure also relates to a laminate for an absorbent article comprising a first substrate comprising intermittent integrally formed protrusions and unformed areas between the intermittent integrally formed protrusions, wherein the protrusions are formed substantially from the first substrate, and wherein the first substrate has a first width and a second substrate joined to the first substrate, the second substrate having a second width, wherein the second width is greater than the first width. The first substrate may be joined to the second substrate in the formed areas and/or in the unformed areas.

These and other features, aspects, and advantages of various embodiments will become better understood with reference to the following description, figures, and claims.

BRIEF DESCRIPTION OF THE DRAWINGS

Many aspects of this disclosure can be better understood with reference to the following figures.

Figure 1:
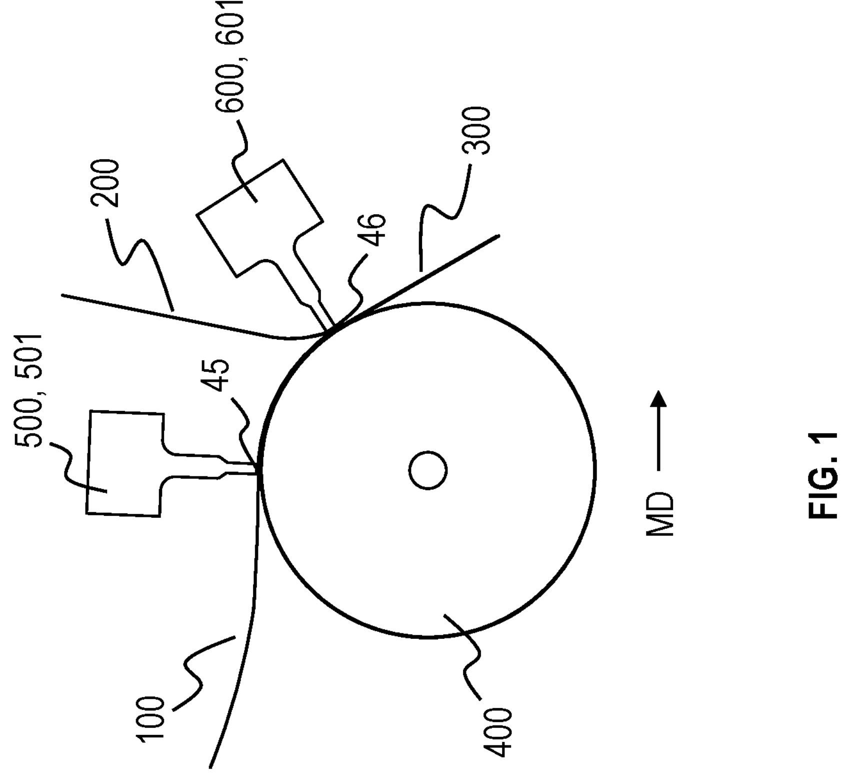
FIG. 1 is an example illustrating a schematic side view of a method and an apparatus for forming a laminate.

It should be understood that the various embodiments are not limited to the examples illustrated in the figures.

DETAILED DESCRIPTION

Introduction and Definitions

This disclosure is written to describe the invention to a person having ordinary skill in the art, who will understand that this disclosure is not limited to the specific examples or embodiments described. The examples and embodiments are single instances of the invention which will make a much larger scope apparent to the person having ordinary skill in the art. Unless defined otherwise, all technical and scientific terms used herein have the same meaning as commonly understood by the person having ordinary skill in the art. It is also to be understood that the terminology used herein is for the purpose of describing examples and embodiments only, and is not intended to be limiting, since the scope of the present disclosure will be limited only by the appended claims.

All the features disclosed in this specification (including any accompanying claims, abstract, and drawings) may be replaced by alternative features serving the same, equivalent, or similar purpose, unless expressly stated otherwise. Thus, unless expressly stated otherwise, each feature disclosed is one example only of a generic series of equivalent or similar features. The examples and embodiments described herein are for illustrative purposes only and that various modifications or changes in light thereof will be suggested to the person having ordinary skill in the art and are to be included within the spirit and purview of this application. Many variations and modifications may be made to the embodiments of the disclosure without departing substantially from the spirit and principles of the disclosure. All such modifications and variations are intended to be included herein within the scope of this disclosure. For example, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All numeric values are herein assumed to be modified by the term "about," whether or not explicitly indicated. The term "about" generally refers to a range of numbers that one of skill in the art would consider equivalent to the recited value (for example, having the same function or result). In many instances, the term "about" may include numbers that are rounded to the nearest significant figure.

In everyday usage, indefinite articles (like "a" or "an") precede countable nouns and noncountable nouns almost never take indefinite articles. It must be noted, therefore, that, as used in this specification and in the claims that follow, the singular forms "a," "an," and "the" include plural referents unless the context clearly dictates otherwise. Thus, for example, reference to "a support" includes a plurality of supports. Particularly when a single countable noun is listed as an element in a claim, this specification will generally use a phrase such as "a single." For example, "a single support."

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

In this specification and in the claims that follow, reference will be made to a number of terms that shall be defined to have the following meanings unless a contrary intention is apparent.

"Disposed on" refers to a positional state indicating that one object or material is arranged in a position adjacent to the position of another object or material. The term does not require or exclude the presence of intervening objects, materials, or layers.

"Absorbent article" refers to devices that absorb and contain bodily exudates, and more specifically, refers to devices that are placed against or in proximity to the body of the wearer to absorb and to contain various bodily exudates discharged from the body.

"Align" or "aligned" or "aligning" means to place or to arrange in a straight line. Aligning edges of substrates, therefore, means arranging the substrates so that the edges in question extend along approximately the same line. It is to be appreciated that aligning edges of substrates can be accomplished in a variety of ways, including placing the substrates one on top of the other or side by side.

"Facing relationship" refers to a relative positioning of materials, such as substrates, in which a surface of one material is oriented toward a surface of another material. For example, when two substrates are stacked on top of each other, they are in a facing relationship. The term does not require or exclude the presence of intervening objects, materials, or layers.

"Machine direction" (MD) refers to the direction of material flow through a process. In addition, relative placement and movement of material can be described as flowing in the machine direction through a process from upstream in the process to downstream in the process.

"Cross direction" (CD) refers to a direction that is generally perpendicular to the machine direction.

"Nip" refers to a space or a gap between two structures. For example, a nip may be formed between an anvil roll and a sonotrode. One or more substrates may be conveyed through such a nip.

"Nonwoven" refers to nonwoven laminates that may comprise melt-blown, carded or other film layers in addition to or instead of spunbonded layers.

General Discussion

Various configurations involve the introduction of a second substrate intermediate two sonotrodes. The first substrate may be narrower or wider than a second substrate. The first substrate may be chosen to improve quality, reduce failure modes, or to enable higher line speeds. The first substrate may have a high basis weight. The first substrate may be a film, nonwoven, or laminate. Portions of the first substrate may fill the hook cavities in a mold roll. A membrane formed intermediate protrusion sites by this first substrate may be thin. When a film is used, the first substrate may be nominally continuous, without fibers. This continuous substrate may avoid a known issue of poor fiber-fiber bonds within a protrusion, which may occur when related art nonwoven substrates are utilized as the precursor material. In the related art, constituent fibers of a nonwoven substrate may only partially or weakly bond together during unitary formation in a protrusion region, a membrane region or at the junction between protrusion and membrane regions. A second substrate may then be introduced adjacent the first substrate, while the first substrate is on the first mold roll. This second substrate may be a nonwoven, film, or laminate. The basis weight of the second substrate may be reduced or lower than the first substrate, as the first substrate may provide a substantial proportional of material to form hooks. In embodiments in which the second substrate is a reinforcement film or nonwoven, the second substrate may have a higher basis weight that the first substrate. A second sonotrode may bond the second substrate to the first substrate. Said bonding may comprise melting, and re-solidification, mechanical entanglement, or a combination of mechanisms. The first substrate to second substrate attachment region may be larger than a cross-sectional area of the protrusions. Forces from the protrusions, which may be hooks, may be spread over a larger area at the transition from first to second substrates. Said second substrate may fill voids intermediate fibrous regions of said first substrate. Said second substrate may act to increase a compressive and/or shear stress in said first substrate, which may enhance bonding intermediate fibers of said first substrate, second substrate, or multiple substrates. Said mechanisms may also affect the membrane region intermediate protrusions, improving inter-fiber bonds and/or forming a membrane where more or all individual fibers are converted into a film-like region. A higher hook force before failure of the hook or failure of the substrate may thus be enabled.

An advantage of the method and apparatus according to various configurations is that a first substrate comprising a high basis weight film may be preheated more than a nonwoven substrate. For example, the first substrate may be heated and/or compressed prior to ultrasonic formation of hooks. Heating may be from a first side, a second side, or both sides of the substrate. Heating may be via convective heat transfer, such as from hot air blowers. Heating may be via radiative heat transfer, such as via radiative infrared heaters. Heating may be via conductive heat transfer, such as via a separate heated roll or a heated mold roll. Mold roll or separate heated roll heating may be via resistive electrical heating internal to the roll, inductive heating, or other methods. Preheating may comprise applying ultrasonic, vibratory, or compressive energy to a first side of a substrate and utilizing a smooth region of a cylindrical anvil roll on a second side. The hot air heaters or other heating means may elevate the substrate to a temperature at which the substrate is softened. The preheat temperature may be just below a melting temperature of the substrate. Where a compressive force is applied to the substrate, non-woven or other fibrous elements in the first substrate may be fully or partially bonded together and may fully or partially form a continuum solid, such as a film.

With the benefit of a dedicated first substrate for the hook formation, a higher preheat temperature may be possible, which may aid hook formation. In some cases, a first side may be heated to or past a softening or melting point, with a second side remaining in a solid phase for transport. In some cases, a first side and/or a second side may be heated to or past a melting point, with a core region intermediate the first and second sides remaining in a solid phase for transport. It is known from testing that heating of a nonwoven substrate tends to result in uneven shrinkage, melting, and wrinkling. Utilizing a film substrate may mitigate these issues.

The first substrate may comprise a film, a nonwoven, a nonwoven with film layers, or other laminates. The first substrate may comprise a film with fibrous reinforcement, the reinforcement may comprise polymer fibers, a nonwoven, cellulose, or cellulosic fibers. The first substrate may comprise a nonwoven comprising at least one bi-component fiber. The bi-component fiber may comprise a first chemical species in a core region and a second chemical species in a sheath region. In alternate embodiments, the first and second chemical species may be disposed side by side, islands in the sea, eccentric, as sheets, or in other geometric relationships. The chemical species may comprise polyethylene (PE), polypropylene (PP), polyethylene terephthalate (PET), polyvinyl alcohol (PVA), or a variety of other polymers. The bi-component fiber may comprise a PE sheath adjacent a PP core. The bi-component fiber may comprise a PP sheath adjacent a PET core. The softening temp, glass transition temperature (Tg), and/or melting temperature of a first component may be different than the softening temp, Tg, and/or melting temperature of a second component. In some embodiments, a first component may comprise a film and second component may comprise a nonwoven. In some embodiments, a PE and/or PP film may be reinforced with PET fibers, which may have a melting, Tg, and/or softening temp higher than the PE or PP film.

The first substrate may comprise a nonwoven material, which may be flattened into a film in a region. The flattened region may comprise a discrete region corresponding to a hook patch, a discrete region larger in a machine direction MD, a cross-direction CD, or both than a hook patch, a region smaller than a final hook patch in one or more dimensions. The flattened region may comprise one or more continuous strips in a machine direction. In some embodiments, a PP/PET Bi-component fiber nonwoven may be flattened into a PP film reinforced with PET fibers. In some embodiments a bi-component fibrous nonwoven comprising components with different melting temperatures may be consolidated into a matrix of fibers in a binder material. The flattening method may comprise pressure, vibrational energy, ultrasonics, and/or heat application (e.g., via conductive, convective, or radiative means). The flattening may occur over an entire substrate, in a machine direction MD region, in a cross-direction CD region, in a discrete region, or in a non-symmetrical shaped region. The discrete regions may be aligned in a machine direction MD and or cross-direction CD with at least one subsequent hook formation, protrusion formation, or bonding operation. The flattening may occur fully or partially via compression of the first substrate against a mold roll or first device. The flattening may occur in a separate step, such as between two rolls. Flattening may occur between smooth rolls, a patterned roll and a smooth roll, and/or between two patterned rolls. In some embodiments, the flattened region may comprise a plurality of regions in the machine direction MD or cross-direction CD, the flattened regions may correspond with protrusion formation regions in a mold roll or first device. Said differently, the protrusion or hook formation pattern may be chosen to correspond with a thermal bond flattened pattern in precursor nonwoven. Thus, the flattening step may occur on a separate machine as a precursor to hook formation. In other embodiments, flattening may be against a mold roll or first device.

A film substrate for hook formation may not be preferred in some product applications. The film substrate with hooks may be further improved by bonding to a second substrate, which may be a carrier nonwoven or laminate. The second substrate may be wider in a cross-direction CD than the first substrate. The second substrate may be longer in a machine direction MD than the first substrate. The second substrate may have a machine direction MD length per product the same, shorter, or longer than a machine direction MD length of a region of protrusions. One or a plurality of lanes of first material and/or protrusion regions may be bonded to a second substrate.

The second substrate may be bonded directly to the first substrate via a second sonotrode while hooks or protrusions of the first substrate are within recesses of the first device or mold roll. A mold roll may be defined as a rotating cylinder with a plurality of recesses for forming protrusions and/or hooks. In some embodiments, one or more mold roll elements may be replaced by flexible mechanical elements, such as an endless loop conveyor belt with a plurality of recesses to form protrusions. In some embodiments, an intermittent stamping process may be utilized in place of continuous rolls or belts. The second sonotrode may be a blade sonotrode or a rotary sonotrode. The second substrate may form a film patch proximate the first substrate. Where a nonwoven or laminate second substrate is utilized, the second substrate may form a film in a second patch region proximate a first patch region formed at the first sonotrode. The first and second substrate layers may intermix and/or entangle in the patch region(s).

The second substrate may be preheated from a first side, a second side, or both sides. The second substrate preheating may be conductive, convective, and/or radiative. The preheating may be via hot air blown against or through a substrate. Blowing air through a substrate for heating may be known from general art as applied to through air drying. The second substrate may be air permeable or air impermeable. Where the second substrate is air impermeable, blowing air through the substrate may not be practical. Preheating may comprise blowing air upstream, downstream, or across one or more sides of the second substrate. The second substrate may be heated to a temperature higher than a Tg, below a melting temperature, near or above a softening temperature.

The first substrate may also be heated upstream the second sonotrode and/or intermediate first and second sonotrodes, the heating may comprise a hot air blast, convective heat transfer, radiative heat transfer, incident infrared (IR) energy, conductive heat transfer, heater elements in a mold roll or first device, inductive heating of the mold roll or first device, or other means. The first substrate may be cooled by conductive heat transfer to the first sonotrode, especially where the first sonotrode is cooled. The preheat temperature of the second substrate may in a softening range and/or may be under a melt temperature. As the first substrate is supported by the mold roll or first device, the temperature of at least a portion of the first substrate may be above a softening temperature, below a melting temperature, at a melting temperature, or above a melt temperature of the first substrate. Alternately, the temperature of at least a portion of one side of the second substrate may be above a softening temperature, below a melting temperature, at a melting temperature, or above a melting temperature of the second substrate. Once the first hooks are formed, structural integrity of the first substrate may no longer be required. Phase transformation from solid to liquid of portion or all of the second substrate may be preferred, especially where the second substrate is a nonwoven and flow of the first substrate around fibers of the second substrate is desired. The bonding between first substrate and second substrate may comprise mechanical entanglement, interdiffusion, melting and re-solidification, or a combination of such methods. The first substrate preheat may be applied to a patch region and/or a region intermediate or adjacent to patches. The pre-heat may serve to bond the first substrate to the second substrate intermediate patches. The preheat may melt the first substrate intermediate patches, which may then be absorbed by the second substrate. A roller, a profiled intermittent roller, a knife or scraper element may be utilized instead of or in conjunction with heating to separate the patch regions into discrete patches and/or to decrease the thickness of membrane or basis weight of first substrate intermediate hook patches. The first substrate may be melted and squeezed out of the regions intermediate hooks and built up in the desired hook patches. The first substrate material intermediate discrete patches may be removed via vacuum, a scrubbing action from the second substrate, or other means. A portion of first substrate material may be recycled into the hook making process. The first substrate may comprise a continuous substrate at a substantially constant flow rate, discrete patches of a first substrate, or a time varying supply of a continuous substrate.

In some embodiments, the first sonotrode may be a blade sonotrode. In other embodiments, the first sonotrode may be a rotary sonotrode. The rotary sonotrode may comprise a rotary sonotrode with support means, such as bearings, disposed on a first and second position with a working surface of the sonotrode intermediate the supporting means. The rotary system may exhibit high compression forces, such as 1 kN, 3 kN, 5 N, or 10 kN per patch. Discrete materials may be added to the material infeed. In practice, the different thicknesses of material are difficult, as the substrates may slide relative to each other in the formation process. By separating the formation into two stages, the relative sliding, mis-tracking, and wrinkling inherent in combining multiple layers with rotary formation may be avoided. The first material may be continuous or may be separated into a series of patches upstream the first sonotrode. Such separation may be a knife, a punch, a die cutter, a laser cutter, or a "perf and pop" operation. A "perf and pop" operation may be defined as making a plurality of intermittent cuts in a substrate along a first line or curve to weaken the substrate and then applying tension or shear to separate the substrate substantially perpendicular to the weakened region. The mold roll may serve to sever a region of first substrate from a continuous length of first substrate to form a patch. The severing means may comprise a knife, a rotating knife, a rotating knife region of the mold roll, an effect of high temperature, an effect of the ultrasonics or other means. The severing may be straight or shaped. The severing may be proximate a patch edge or spaced apart from a patch perimeter region. A key to realizing a discrete intermittent first stage may be to utilize a rotary sonotrode. A rotary sonotrode may draw in the patch, whereas the patch may jam at the infeed edge of a blade sonotrode. In some embodiments, the need for a separate second substrate may be avoided by feeding the first substrate and the second substrate positioned adjacent each other into a rotary sonotrode against a mold roll or first device. The first substrate may have a cross-direction CD width smaller than, equal to, or larger than the patch. The first substrate may have a machine direction MD length shorter than, equal to, or longer than the patch. Severing of discrete patches may utilize a knife element and/or die cutter element against a sonotrode, which may be a rotary sonotrode. Discrete patches of first substrate may be held in a positional relationship with the mold roll or first device by vacuum, mechanical actuators, endless belts such as hold down belts, or electrostatic forces. The first and second substrates may be preheated and may be preheated to different temperatures.

Where a cutting or separating operation is utilized, the first substrate may be preheated at or above a softening temperature, or preheated near, at, or above a melting temperature intermediate cutting and a sonotrode. The first substrate may be preheated before cutting, and then applied to a mold roll or first device. The mold roll or first device may be preheated, such that first substrate partially melts on the mold roll or first device. The preheating of the mold roll first device may be a surface heating, such as via hot air, inductive heating, or resistance heating which affects only a thin periphery region of the mold roll or first device. The differently, the mold roll or first device preheating may be a skin effect.

In some embodiments, a flattening step may be utilized in lieu of or complementary to a first sonotrode. For example, instead of a rotary sonotrode, a rotating cylinder or a rotating tooling with a cylindrical region may force a first substrate at least partially onto a mold roll or first device. The first substrate may be preheated. The first substrate may be intermittent via any of the methods defined above. The flattening element may be heated to a temperature, which may be near, at, or above a melting temperature of the first substrate.

Where a flattening, a sonotrode, or other pre-processing of a substrate is utilized, a plurality of lanes of flattened or other preprocessed regions may be created in a substrate. The lanes may then be separated into a plurality of webs via any means common in the industry, such as via a slitting, die-cutting, or breaking at a perforation line. A single or reduced number of flattening machine components may thus serve several lanes of second sonotrodes. In some embodiments, the flattening may comprise a first sonotrode which creates partially formed protrusions in a first substrate. For example, a first sonotrode may form a thin membrane with hemi-spherical protrusions using a first mold roll. The partial protrusion formations may then be aligned with a finished hook shape recess, or other protrusion shape, in a second mold roll. Intermediate the two the mold rolls, the first substrate may be separated into a plurality of lanes of continuous or discrete material. The separation may comprise slitting, die cutting, laser cutting, an intermittent knife, or perforating.

In some embodiments, the first sonotrode may be replaced by one or more compression rolls, which may be heated. The compression roll may be followed by a blade or rotary sonotrode. The compression rolls may comprise a full cross-direction CD width of the first substrate, a width of the hook patch, or a width greater than a hook patch by a spacing width. The compression rolls may be rubber, steel, metal, ceramic, and/or other material. The compression rolls may have a shape, which may match a patch shape, be larger than a patch shape by a buffer amount or have a shape partially circumscribing or inscribing the patch shape. The heated compression rolls may be more cost efficient than multiple sonotrodes per lane of substrate.

In some embodiments, bond sites may be disposed intermediate hook formation patches. Where the second substrate is combined with the first substrate via a second sonotrode, the first and second substrates may not be bonded together for a machine direction MD length. By adding bond sites in this region, the two materials may form a laminate without unbonded free ends. The bond sites may be disposed intermediate bond sites in a machine direction MD and/or an cross-direction CD disposition. The bond sites intermediate patches in a cross-direction CD position need not extend the full range through the cross-direction CD but may extend proximate an edge of the first or second materials. Stated differently, bond sites may bond any free lateral edges of the first material and/or any free longitudinal free edges of the first material to the second material. The bond sites may be formed by raised regions intermediate hook patch regions on a mold roll. The bonding may be via bonding nubs, bars, or shaped elements. The bonding elements may have a radius the same as, less than, or greater than a radius of a periphery portion of a protrusion or hook formation region. The bonding elements may form bond sites intermediate hook or protrusion formation regions. The bond sites may form a consolidated or film-like region. The bond sites may form a grommet around a periphery of the bond sites. The grommet or consolidated regions may comprise a mechanical entanglement, a melting and re-solidification, an interdiffusion, or other bonding mechanisms. In some embodiments, a second heating means intermediate first and second sonotrodes may at least partially bond the first and second substrates.

A hook may be formed from two substrates. A first substrate may partially or substantially fill a hook cavity. The first substrate may completely fill the hook cavities. The first substrate may form a membrane layer in a patch region, which may be connected to a second substrate. The first substrate membrane layer may provide structural integrity to the protrusion against tangential or normal forces, such as may be experienced in use as a hook and loop fastener system. The first substrate may be a cross-direction CD strip with a width similar to a patch cross-direction CD width. A plurality of first elements may be provided against a plurality of patches on a mold roll or first device. A plurality of ultrasonic bonds may be formed intermediate patches of protrusions.

A first substrate may be highly beneficial to secondary fasteners, as it may enable a thin high-strength film substrate to be positioned in a cross-direction CD strip with a hook patch, which may be shaped. A second substrate in this use case may comprise a landing zone material of a diaper, which may commonly have large loops of material. High basis weights of landing zone material to facilitate good hook formation may be cost prohibitive. Separating the hook formation may enable a relatively narrow strip of high basis weight film to enable hook formation with a relatively low basis weight of landing zone to minimize product cost. Separating hook formation from landing zone may reduce the complex performance requirements of each functional material, thus enabling a wider range of constituent materials. The separate first substrate may provide a different color, surface texture, transparency, or other visual insignia or aesthetic relative to the base material. Bond sites intermittent patches of hooks used as secondary fasteners may provide an integrated appearance and/or prevent, or inhibit, delamination. Alternately, the discretized first substrate may enable a reduced usage of first substrate. Where a discrete substrate is utilized, a region of bond sites proximate a hook patch may be utilized to maintain a holistic appearance and functional strength. The bond sites may be positioned proximate corners or edges of a discrete patch, which may be rectangular, to mitigate risks of perceived rough edges in a finished product. The mitigation may comprise crushing the corners or edges to eliminate rough edges.

In some embodiments, instead of a narrow first substrate and a wide second substrate, the first substrate may be wide and the second substrate narrow. For example, the first substrate may be a non-woven, which may be pressed into a plurality of cavities in a mold roll. Protrusions such as hooks may be formed by this process. A second, narrow substrate may be introduced adjacent a second surface of the first substrate. The second substrate may be a film, high basis weight non-woven, laminate, and/or liquid polymer. A second bonding step, which may comprise a sonotrode, thermal bonding, crimping, or a combination of methods, may then bond this second substrate to the first substrate. The second substrate may reinforce the base of protrusions, such as hooks. Where the first hook formation step does not completely fill the cavity and/or does not completely bond fibers into a continuum solid, the second substrate may complete a packout process of a plurality of hook cavities. Without being limited by theory, this reinforcement may occur at a higher pressure to cause material flow due to a localized high basis weight region. The laminate formed by this process may have hooks or other protrusions on one side, and a strong reinforcement layer on a second side. The surface of the product outside a hook patch may thus present a soft, aesthetically pleasing non-woven appearance, even when the reinforcement patch is a film or high basis weight non-woven. The aforementioned methods of pre-heat, flattening, discrete patches, partially melting either first or second substrate and other methods disclosed herein apply to this embodiment with a narrow second substrate.

The methods disclosed here are readily applicable to primary fasteners. A first substrate may comprise a film or high basis weight nonwoven to create high strength primary hooks. A second substrate may comprise a nonwoven utilized as a fastener tab. The fastener tab may be continuous or discrete. The fastener tabs may be nested, such that a first and second fastener tab regions are cut from a single strip of nonwoven, film, or laminate. Where primary hook fastener patches are disposed on a substrate in a nested configuration, the hook patches may be disposed in a single line or a plurality of lines. The method disclosed herein of discrete first substrates is well suited to primary fasteners. The method of bonding regions intermediate hook patches or edge regions of discrete hooks is applicable to primary fasteners in products. A discrete first substrate patch on a fastening tab second substrate may prevent or inhibit a rough aesthetic at a cut edge of the fastener tab. In some embodiments, a partial thermal bond may be created in place of or in conjunction with a second ultrasonic bonding step.

The methods disclosed here are suitable for mechanical fasteners utilized in a pants style diaper. For example, refastenable diapers may require a high performance hook. The method of a high localized basis weight of a first substrate in a cross-direction CD region bonded to a wider second substrate, which may be a carrier non-woven or laminate, may create a strip of hooks regions in one or more lanes of a hook laminate. The intermediate laminate containing hooks may be cut into discrete patches and turned, such as 90°, prior to attachment to a diaper web. Such construction may comprise making two lanes of hooks in a first substrate, applying a second carrier nonwoven substrate, bonding the two webs together, cutting the laminate into a patch, turning the laminate patch 90°, spacing the hook containing laminate patch in a machine direction MD along a belted diaper continuous web, bonding the hook containing laminate patch to the belted pant diaper, and cutting between hook elements to create individual diaper pants with a complete waistband and a refastenable element.

Various embodiments may relate to a disposal tape in which the first substrate may be a film, nonwoven, or laminate and the second substrate may be a carrier web. One or more lanes of machine direction MD oriented strips of hooks may be made on a common mold roll or first device. The strips may be continuous or intermittent hooks. The strips may contain shaped elements at edges of intermittent strips. The lanes may be slit, cut, or separated into a plurality of spaced apart substrates. The spaced apart substrates may be wound onto one or a plurality of cores or other transport mechanisms and may subsequently be fed into an absorbent article converting line. Such construction may comprise making at least one region of hooks in a first substrate, applying a second carrier nonwoven substrate, bonding the two webs together, cutting the laminate into a patch, turning the laminate patch 90°, spacing the hook containing laminate patch in a machine direction MD along a absorbent article backsheet, belt or other outward facing region of the absorbent article, and bonding the hook containing laminate patch to the absorbent article. A portion of the carrier may be folded over the disposal hooks before or after application. A portion of the carrier may be folded over the disposal hooks before or after cutting. A portion of the carrier may be folded over the disposal hooks before or after turning.

Feminine hygiene pads may utilize hooks for temporary bonds to a panty, for wing attachment to a pad or panty, to attach disposable liners, or as a quiet and discreet covering layer. These applications may utilize a low basis weight nonwoven material as the second substrate.

The second substrate in many of these product embodiments may have unique properties which make the second substrate unsuitable for unitary hook formation per the methods disclosed in related art. Non-limiting examples may include soft aesthetics or low basis weight. Addition of a region of first substrate chosen to improve hook or other protrusion performance may enable unique combinations and product benefit vectors. A significant advantage may be increased production rate, which may lower product cost. Several of these embodiments are preferentially made as one or a plurality of machine direction MD lanes, which are then cut and turned prior to application and bonding on a product.

Various embodiments relate to the use of printed substrates with graphics or insignia. The methods disclosed here may enable a more aesthetically pleasing graphic appearance, by separating the hook formation process from the lamination of a second substrate to the first substrate. The first substrate may be transparent. The first substrate may be a film, to reduce diffraction at inter-fiber boundaries which may be common in a rotary formed hook patch. Nonwoven or other fibrous pre-cursor substrates may retain a fibrous appearance at a small scale. The second substrate may be printed. The printing on the second substrate may be distorted less by the bonding operation at the second sonotrode. As the hook cavities are already substantially or completely filled at this point in the process, the second substrate may remain flatter at the boundary between substrates.

Bond sites intermediate hook or protrusion regions on a mold roll or first device may have a shape, pattern, or insignia. A second sonotrode and/or heat may be used to form a matching shape the first and/or second substrate.

Various Examples

FIG. 1 is an example illustrating a schematic side view of a method and an apparatus for forming a laminate 300. A first device 400, a second device 500, and a third device 600 may be provided. A first nip 45 may be formed between the first device 400 and the second device 500. A second nip 46 may be formed between the first device 400 and the third device 600. The first device 400 may be a mold roll. The second device 500 may comprise a first source of vibration energy 501. Similarly, the third device 600 may comprise a second source of vibration energy 601. The second device 500 may be any type of sonotrode, including but not limited to a blade sonotrode (as shown in FIG. 1) or a rotary sonotrode. Similarly, the third device 600 may be any type of sonotrode, including but not limited to a blade sonotrode (as shown in FIG. 1) or a rotary sonotrode. A first substrate 100 may be conveyed in a machine direction MD through the first nip 45. The first source of vibration energy 601 may apply energy to the first substrate 100 in the first nip 45 to cause a portion of the first substrate 100 to be heated adequately to flow into and fill a plurality of shaped recesses on an outer surface of the first device, which will be described in greater detail with reference to FIG. 3. Subsequently, the altered first substrate 100 and a second substrate 200 may both be conveyed through the second nip 46. The second source of vibration energy 601 may apply energy to the second substrate 100 and/or to the first substrate 100 to bond the first substrate 100 to the second substrate 200, thereby forming a laminate 300.

FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N, FIG. 2O, FIG. 2P, FIG. 2Q, FIG. 2R, FIG. 2S, FIG. 2T, FIG. 2U, FIG. 2V, FIG. 2W, and FIG. 2X cooperate to illustrate some non-limiting variations of a method and an apparatus for forming a laminate 300. The first substrate 100 may have a width $W_{100}$ in a cross direction CD. The first substrate 100 may comprise a plurality of strips. A first strip 101 of the plurality of strips may have a width $W_{101}$ in a cross direction CD. A second strip 102 of the plurality of strips may have a width $W_{102}$ in a cross direction CD. The first substrate 100 may comprise a plurality of discrete segments 103. The second substrate 200 may have a width $W_{200}$ in the cross direction CD. The second substrate 200 may comprise a plurality of strips. A first strip 201 of the plurality of strips may have a width $W_{201}$ in a cross direction CD. A second strip 202 of the plurality of strips may have a width $W_{202}$ in a cross direction CD. The second substrate 200 may comprise a plurality of discrete segments 203. The first device 400 may comprise an outer surface 402 having one or more raised portions 406 disposed thereon. The first substrate 100, in any form, may be passed through the first nip 45 formed between the first device 400 and the second device 500. Both the first substrate 100 and the second substrate, in any form, may be passed through the second nip 46 formed between the first device 400 and the third device 600.

According to various configurations, and as shown in FIG. 2A, FIG. 2G, FIG. 2M, FIG. 2S, the first substrate width $W_{100}$ may be equal to the second substrate width $W_{200}$. According to various configurations, and as shown in FIG. 2B, FIG. 2H, FIG. 2N, FIG. 2T, the first substrate width $W_{100}$ may be less than the second substrate width $W_{200}$. According to various configurations, and as shown in FIG. 2C, FIG. 2I, FIG. 2O, FIG. 2U, the first substrate width $W_{100}$ may be greater than the second substrate width $W_{200}$. According to various configurations, the combined widths $W_{101}$, $W_{102}$ of the plurality of strips 101, 102 that make up the first substrate 100 may be less equal than, greater than, or equal to the width $W_{200}$ of the second substrate 200. Preferably, and as shown in FIG. 2D, FIG. 2J, FIG. 2P, FIG. 2V, the combined widths $W_{101}$, $W_{102}$ of the plurality of strips 101, 102 that make up the first substrate 100 are less equal than the width $W_{200}$ of the second substrate 200. According to various configurations, the combined widths $W_{201}$, $W_{202}$ of the plurality of strips 201, 202 that make up the second substrate 200 may be less equal than, greater than, or equal to the width $W_{100}$ of the first substrate 100. Preferably, and as shown in FIG. 2E, FIG. 2K, FIG. 2Q, FIG. 2W, the combined widths $W_{201}$, $W_{202}$ of the plurality of strips 201, 202 that make up the second substrate 200 are less equal than the width $W_{100}$ of the first substrate 100. According to various configurations, and as shown in FIG. 2F, FIGS. 2L, 2R, and 2X, the first substrate 100 may comprise a plurality of strips 101, 102 and the second substrate 200 may comprise a plurality of strips 201, 202.

As previously explained, the second device 500 and/or the third device 600 may be any type of sonotrode, including but not limited to a blade sonotrode or a rotary sonotrode. In configurations wherein the first substrate 100 and/or the second substrate 200 comprises a plurality of discrete sheets 103, 203, it may be preferable for a rotary sonotrode to be employed. As will be shown and discussed hereinafter, the first substrate 100 and/or the second substrate 200 may be prefabricated into the pluralities of discrete sheets 103, 203. The discrete sheets 103, 203 may be cut in-line. The discrete sheets 103, 203 may be transferred through the process via one or more vacuum-assisted rollers, as will be discussed hereinafter.

Figures 2A, 2B:
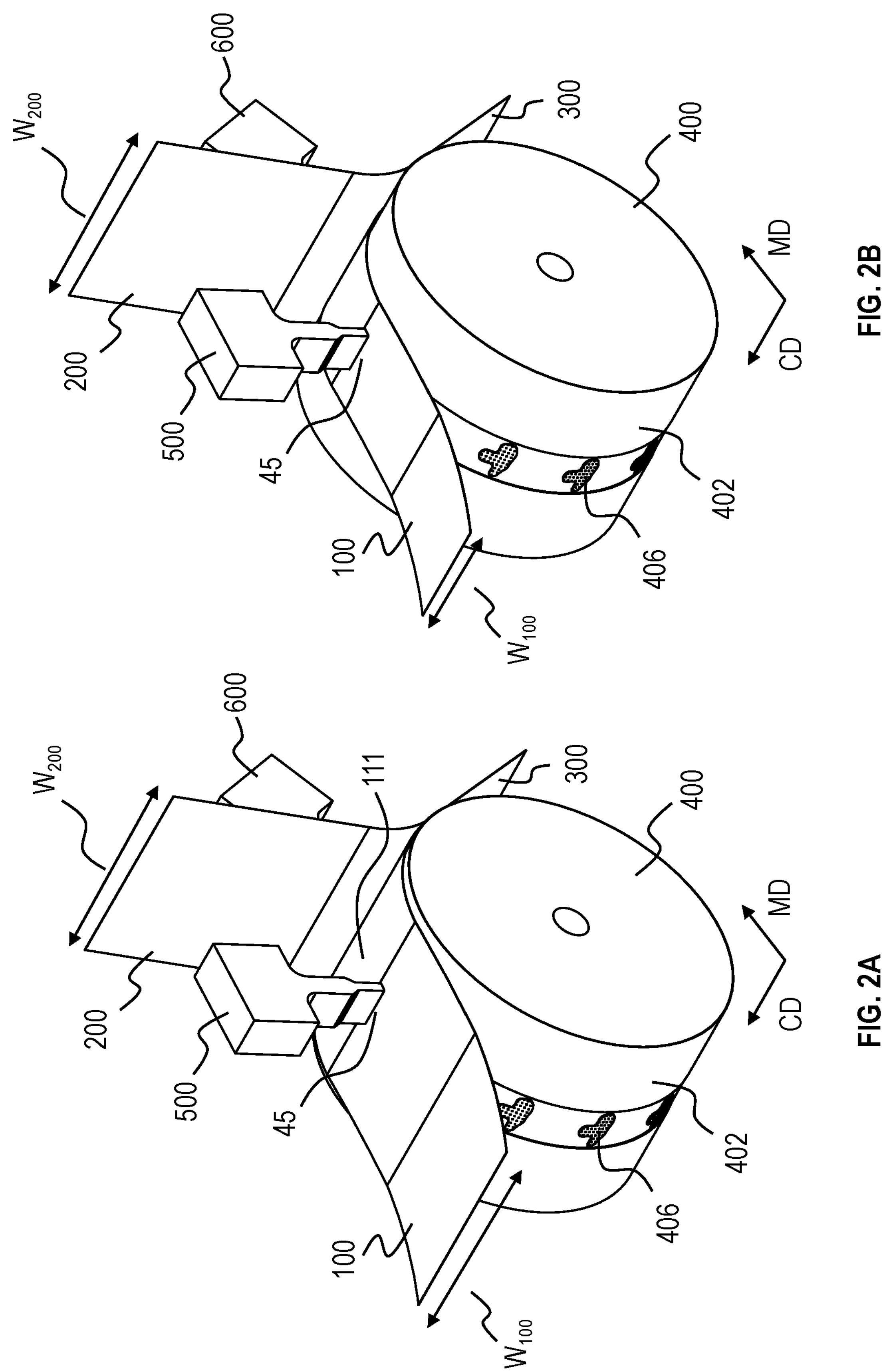
FIG. 2A is an example illustrating a schematic perspective view of the method and the apparatus for forming a laminate from a first substrate and a second substrate, having equal widths.
FIG. 2B is an example illustrating a schematic perspective view of the method and the apparatus for forming a laminate from a first substrate and a second substrate, the first substrate having a width less than a width of the second substrate.
Figures 2C, 2D:
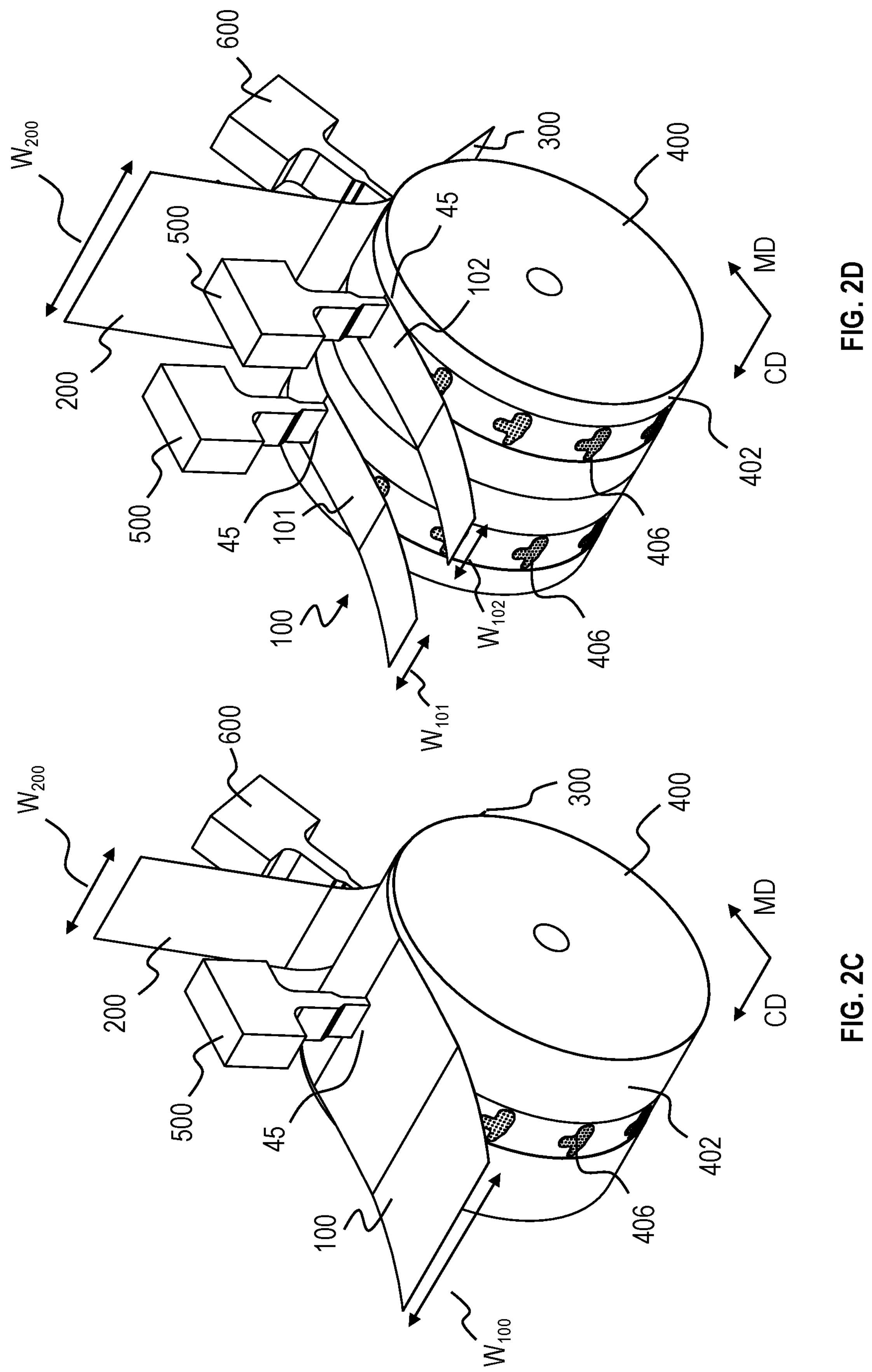
FIG. 2C is an example illustrating a schematic perspective view of the method and the apparatus for forming a laminate from a first substrate and a second substrate, the second substrate having a width less than a width of the first substrate.
FIG. 2D is an example illustrating a schematic perspective view of the method and the apparatus for forming a laminate from a first substrate comprising a plurality of strips and a second substrate.
Figures 2E, 2F:
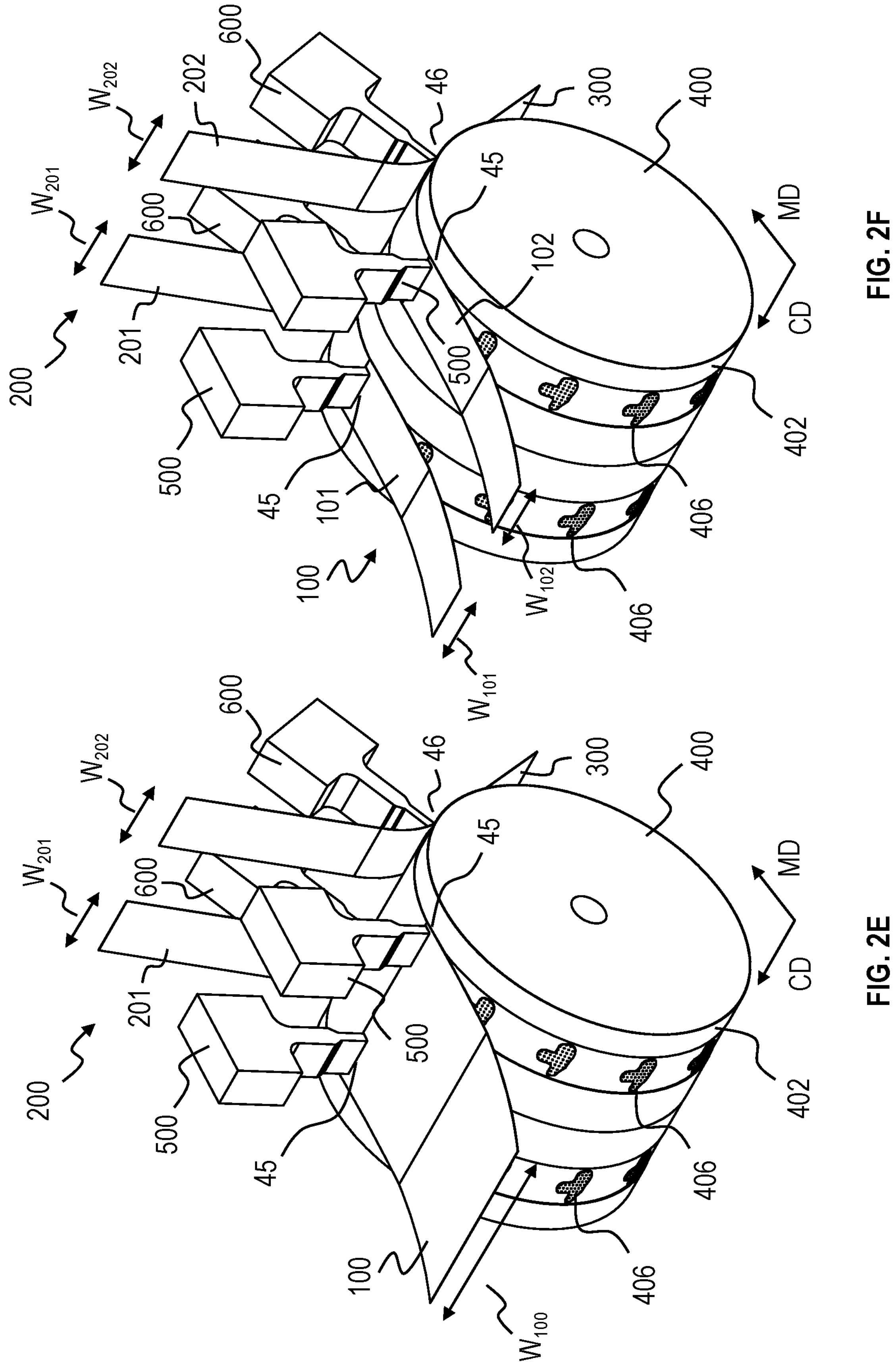
FIG. 2E is an example illustrating a schematic perspective view of the method and the apparatus for forming a laminate from a first substrate and a second substrate comprising a plurality of strips.
FIG. 2F is an example illustrating a schematic perspective view of the method and the apparatus for forming a laminate from a first substrate comprising a plurality of strips and a second substrate comprising a plurality of strips.
Figures 2G, 2H:
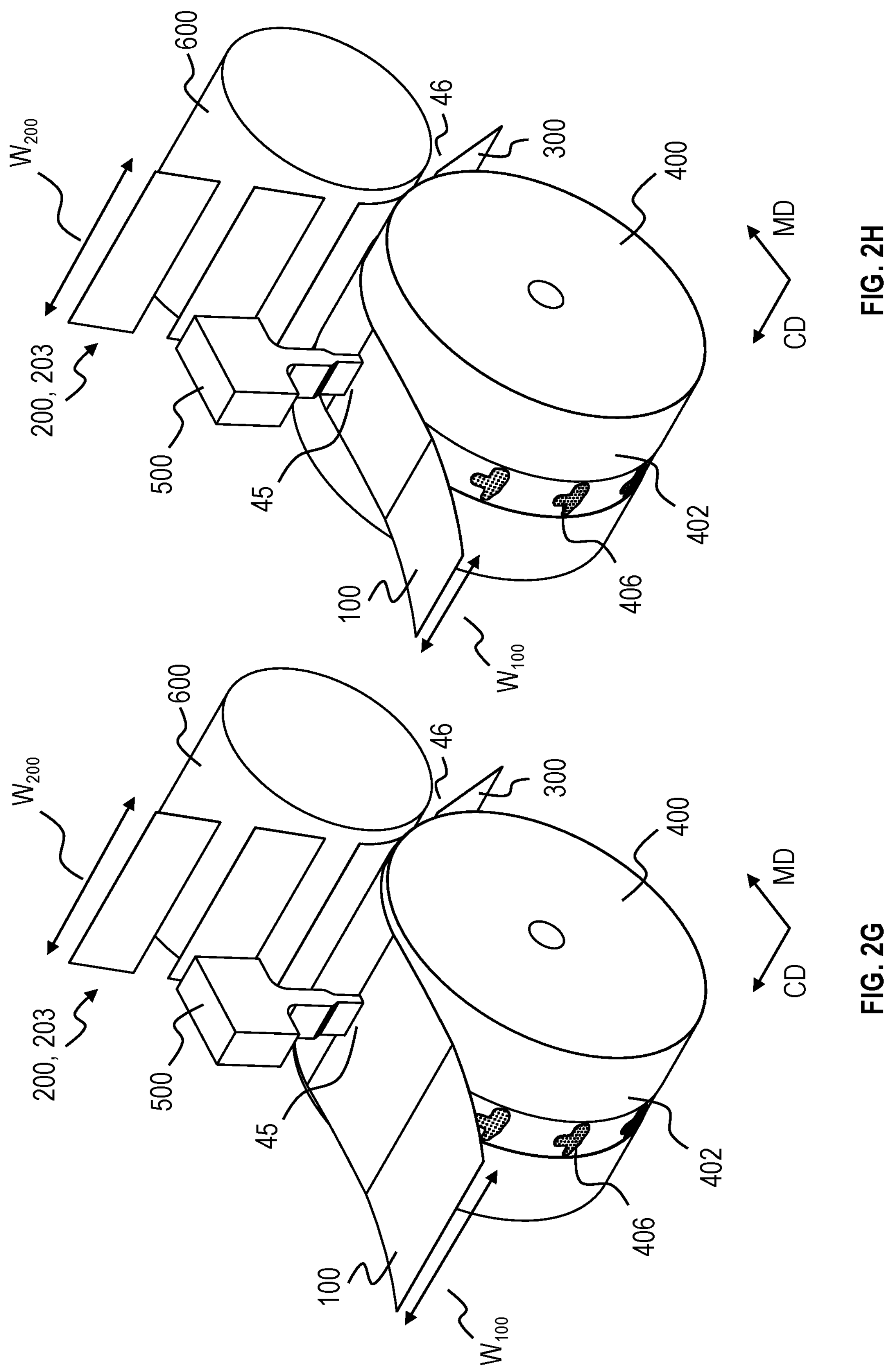
FIG. 2G is an example illustrating a schematic perspective view of the method and the apparatus for forming a laminate from a first substrate and a second substrate, having equal widths, the second substrate comprising a plurality of discrete segments.
FIG. 2H is an example illustrating a schematic perspective view of the method and the apparatus for forming a laminate from a first substrate and a second substrate, the first substrate having a width less than a width of the second substrate, and the second substrate comprising a plurality of discrete segments.
Figures 2I, 2J:
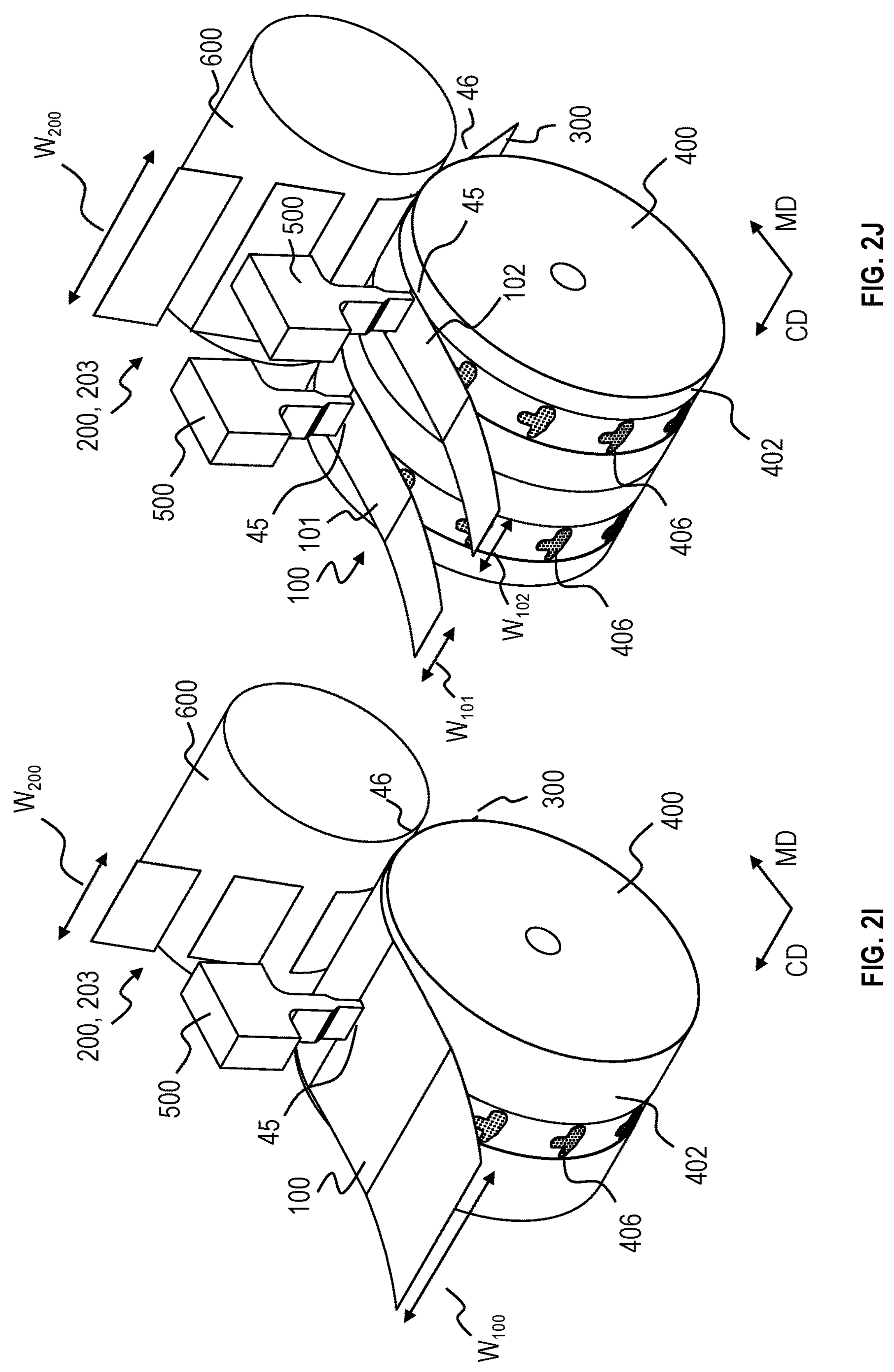
FIG. 2I is an example illustrating a schematic perspective view of the method and the apparatus for forming a laminate from a first substrate and a second substrate, the second substrate having a width less than a width of the first substrate, and the second substrate comprising a plurality of discrete segments.
FIG. 2J is an example illustrating a schematic perspective view of the method and the apparatus for forming a laminate from a first substrate comprising a plurality of strips and a second substrate, the second substrate comprising a plurality of discrete segments.
Figures 2K, 2L:
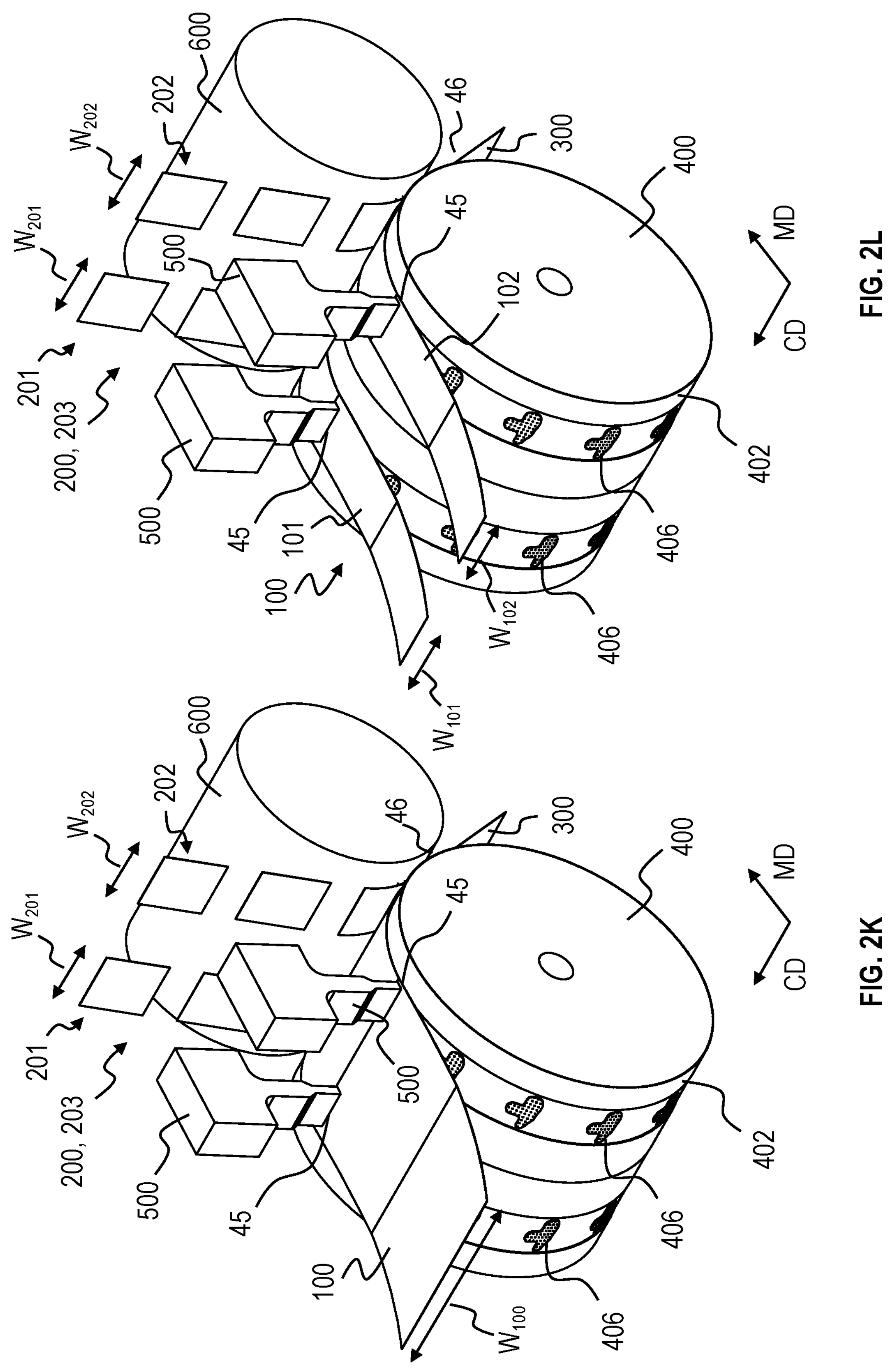
FIG. 2K is an example illustrating a schematic perspective view of the method and the apparatus for forming a laminate from a first substrate and a second substrate comprising a plurality of strips, each strip comprising a plurality of discrete segments.
FIG. 2L is an example illustrating a schematic perspective view of the method and the apparatus for forming a laminate from a first substrate comprising a plurality of strips and a second substrate comprising a plurality of strips, each strip comprising a plurality of discrete segments.
Figures 2M, 2N:
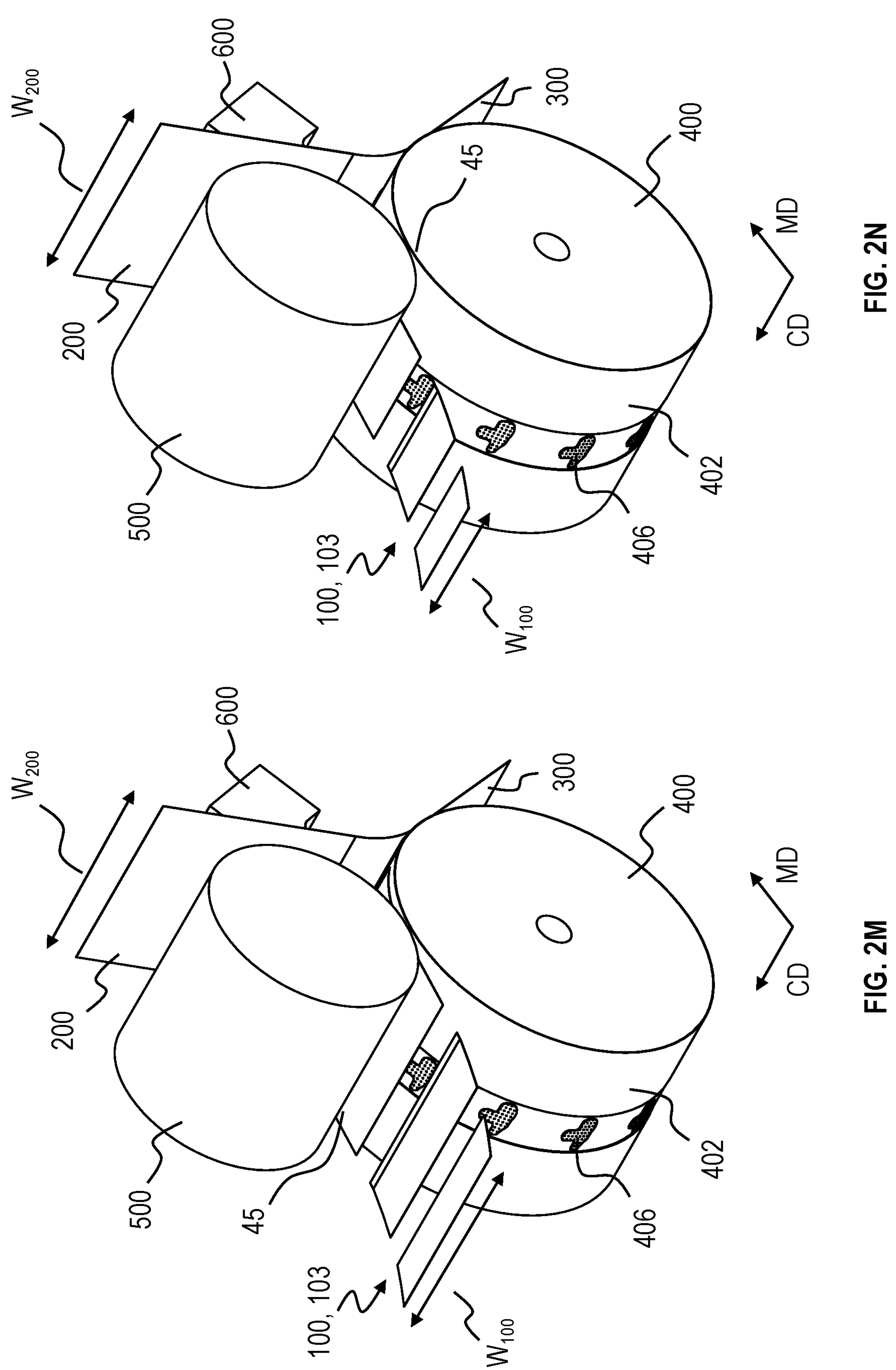
FIG. 2M is an example illustrating a schematic perspective view of the method and the apparatus for forming a laminate from a first substrate and a second substrate, having equal widths, the first substrate comprising a plurality of discrete segments.
FIG. 2N is an example illustrating a schematic perspective view of the method and the apparatus for forming a laminate from a first substrate and a second substrate, the first substrate having a width less than a width of the second substrate, and the first substrate comprising a plurality of discrete segments.
Figures 2O, 2P:
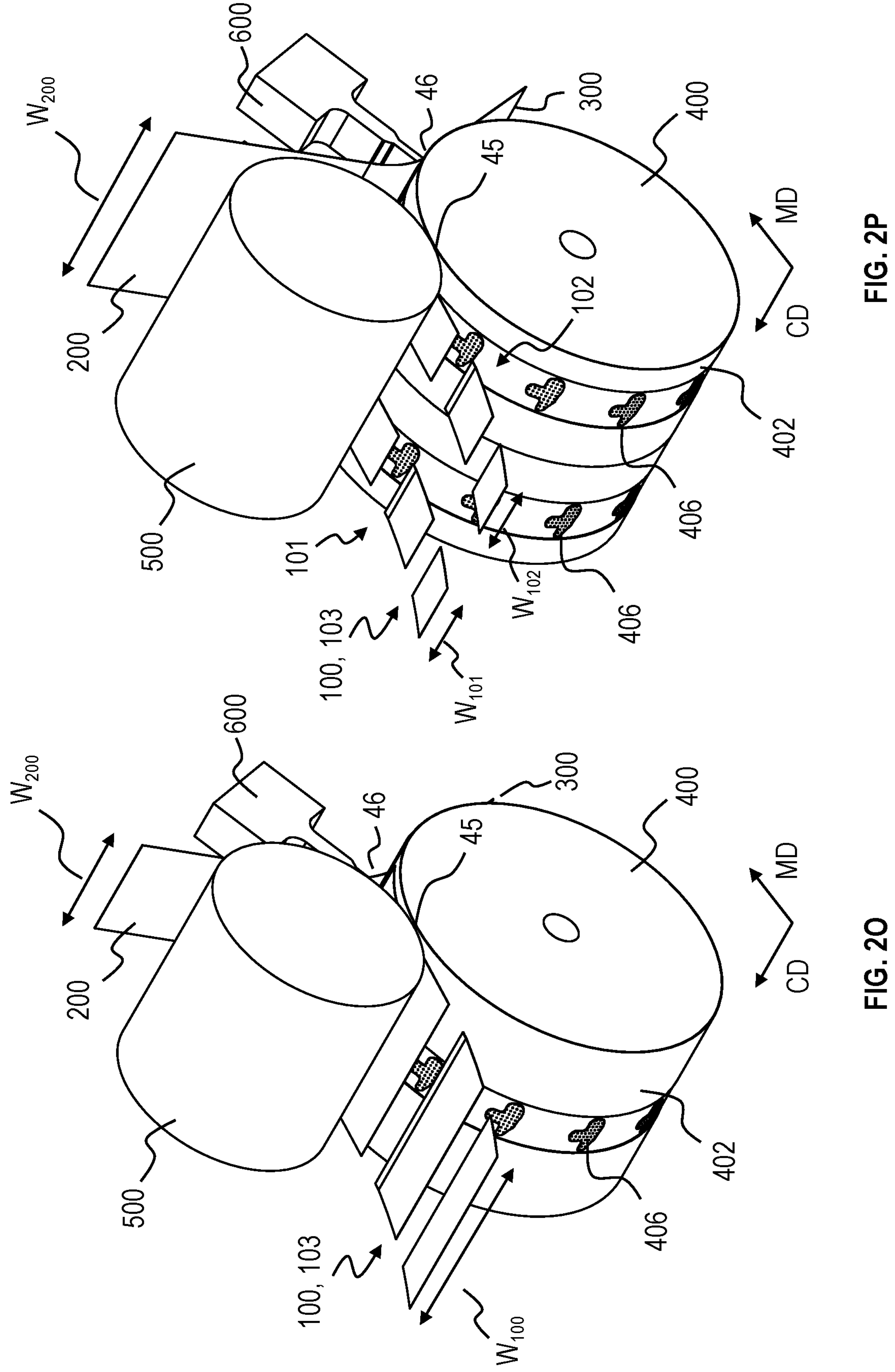
FIG. 2O is an example illustrating a schematic perspective view of the method and the apparatus for forming a laminate from a first substrate and a second substrate, the second substrate having a width less than a width of the first substrate, and the first substrate comprising a plurality of discrete segments.
FIG. 2P is an example illustrating a schematic perspective view of the method and the apparatus for forming a laminate from a first substrate comprising a plurality of strips, each of the strips comprising a plurality of discrete segments, and a second substrate.
Figures 2Q, 2R:
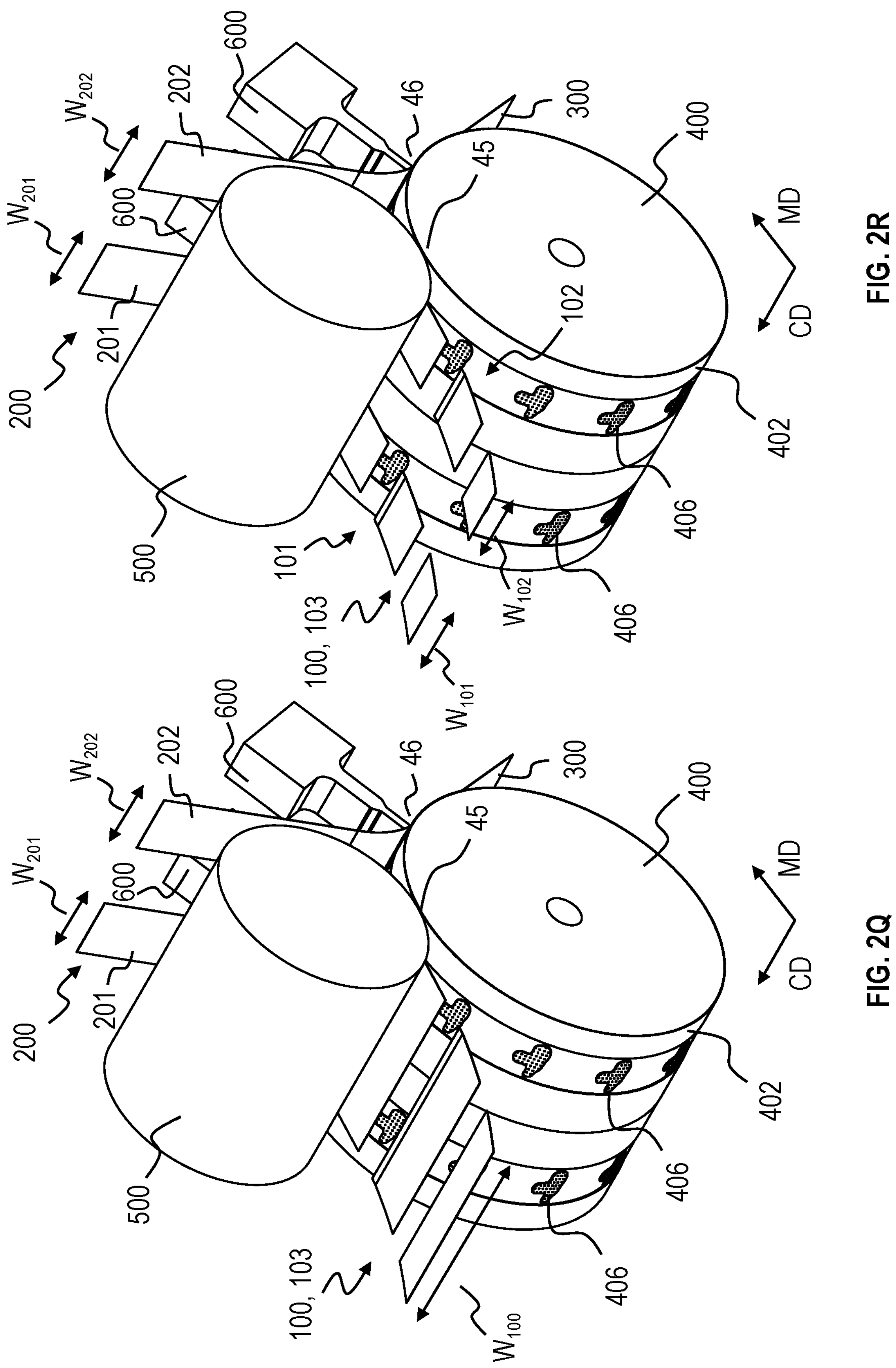
FIG. 2Q is an example illustrating a schematic perspective view of the method and the apparatus for forming a laminate from a first substrate and a second substrate comprising a plurality of strips, and the first substrate comprising a plurality of discrete segments.
FIG. 2R is an example illustrating a schematic perspective view of the method and the apparatus for forming a laminate from a first substrate comprising a plurality of strips, each of the strips comprising a plurality of discrete segments, and a second substrate comprising a plurality of strips.
Figures 2S, 2T:
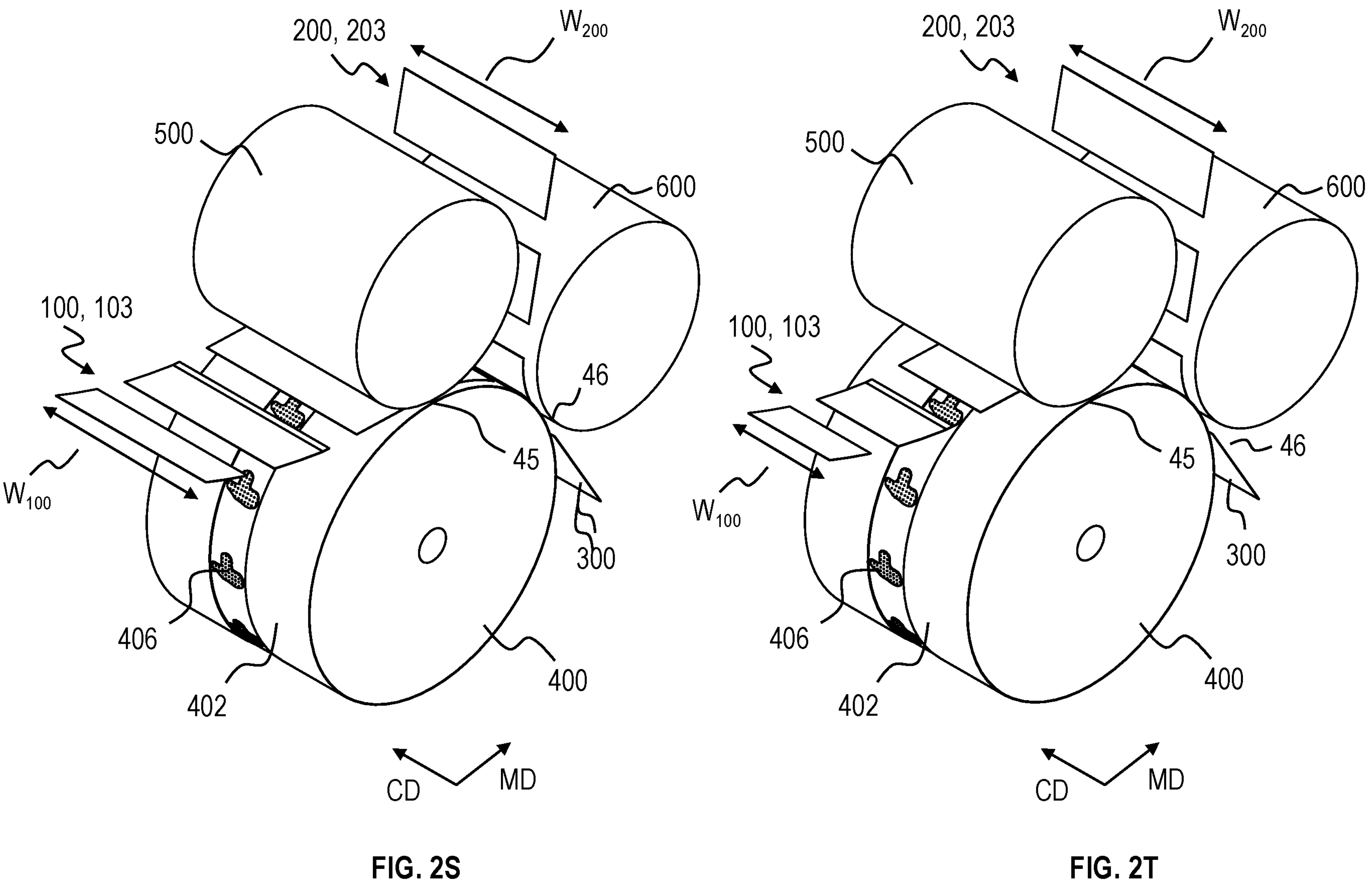
FIG. 2S is an example illustrating a schematic perspective view of the method and the apparatus for forming a laminate from a first substrate and a second substrate, having equal widths, the first substrate and the second substrate each comprising a plurality of discrete segments.
FIG. 2T is an example illustrating a schematic perspective view of the method and the apparatus for forming a laminate from a first substrate and a second substrate, the first substrate having a width less than a width of the second substrate, and the first substrate and the second substrate each comprising a plurality of discrete segments.
Figures 2U, 2V:
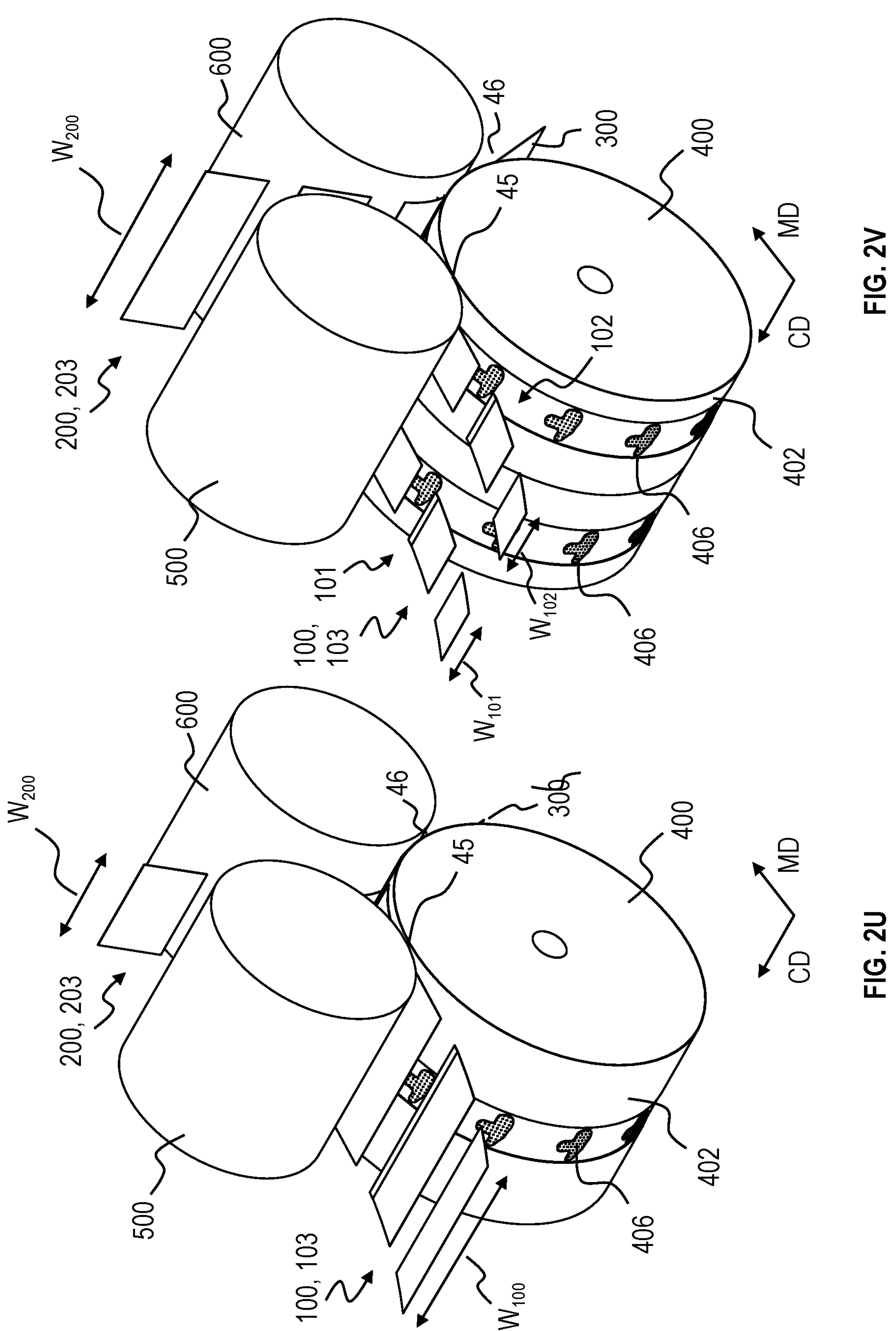
FIG. 2U is an example illustrating a schematic perspective view of the method and the apparatus for forming a laminate from a first substrate and a second substrate, the second substrate having a width less than a width of the first substrate, and the first substrate and the second substrate each comprising a plurality of discrete segments.
FIG. 2V is an example illustrating a schematic perspective view of the method and the apparatus for forming a laminate from a first substrate comprising a plurality of strips and a second substrate, the first substrate and the second substrate each comprising a plurality of discrete segments.
Figures 2W, 2X:
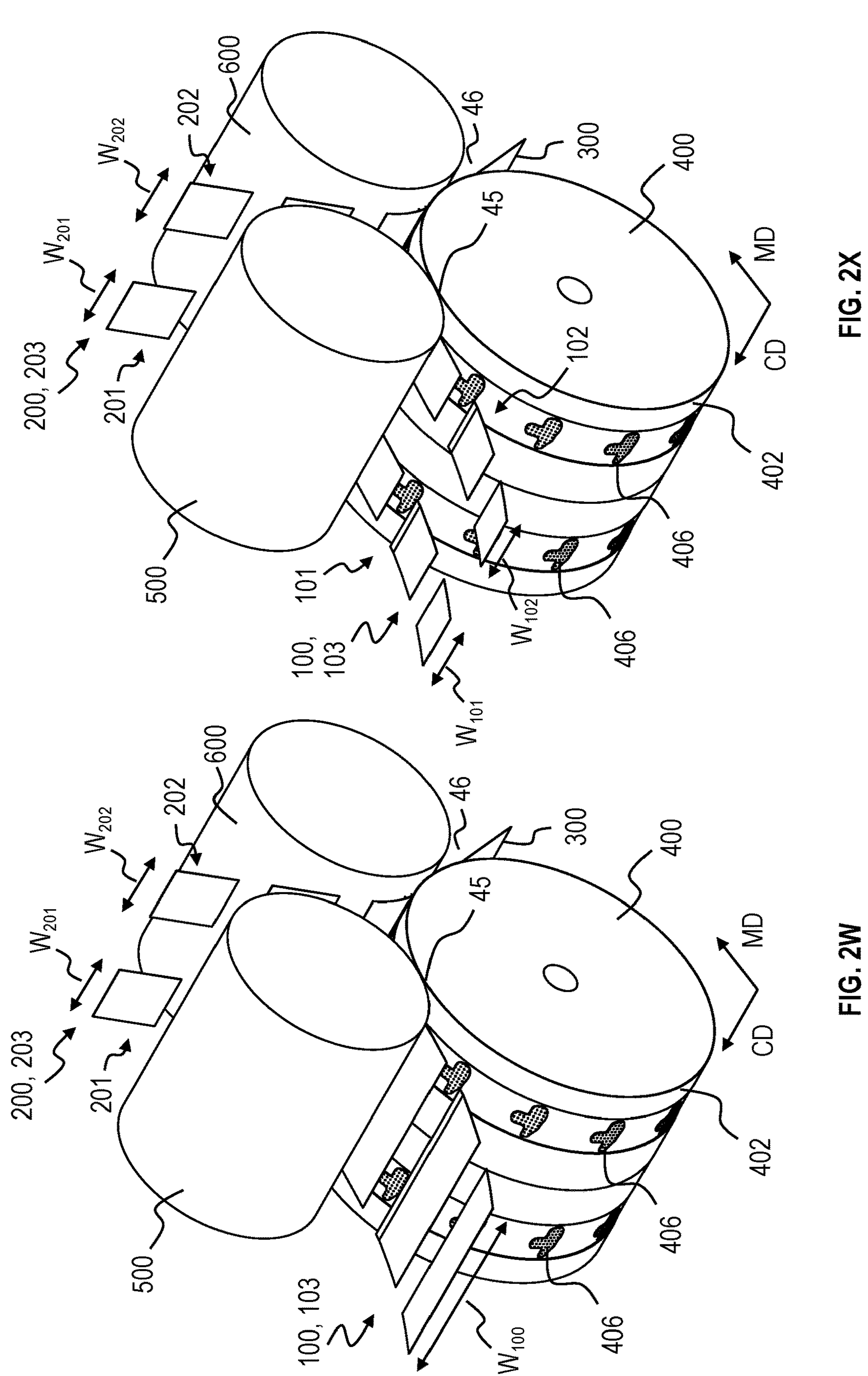
FIG. 2W is an example illustrating a schematic perspective view of the method and the apparatus for forming a laminate from a first substrate and a second substrate comprising a plurality of strips, and the first substrate and the second substrate each comprising a plurality of discrete segments.
FIG. 2X is an example illustrating a schematic perspective view of the method and the apparatus for forming a laminate from a first substrate comprising a plurality of strips and a second substrate comprising a plurality of strips, the first substrate and the second substrate each comprising a plurality of discrete segments.

FIGS. 2A-2X also illustrate that neither the first substrate 100 nor the second substrate 200 need be altered across their entire widths. For example, the first substrate 100 may be altered only along a lane 111 extending in the machine direction MD. The alterations to the first substrate 100 may be intermittently, for example, if an outer surface 402 of the first device 400 comprises raised portions 406 that are spaced at periodic intervals.

Figure 3:
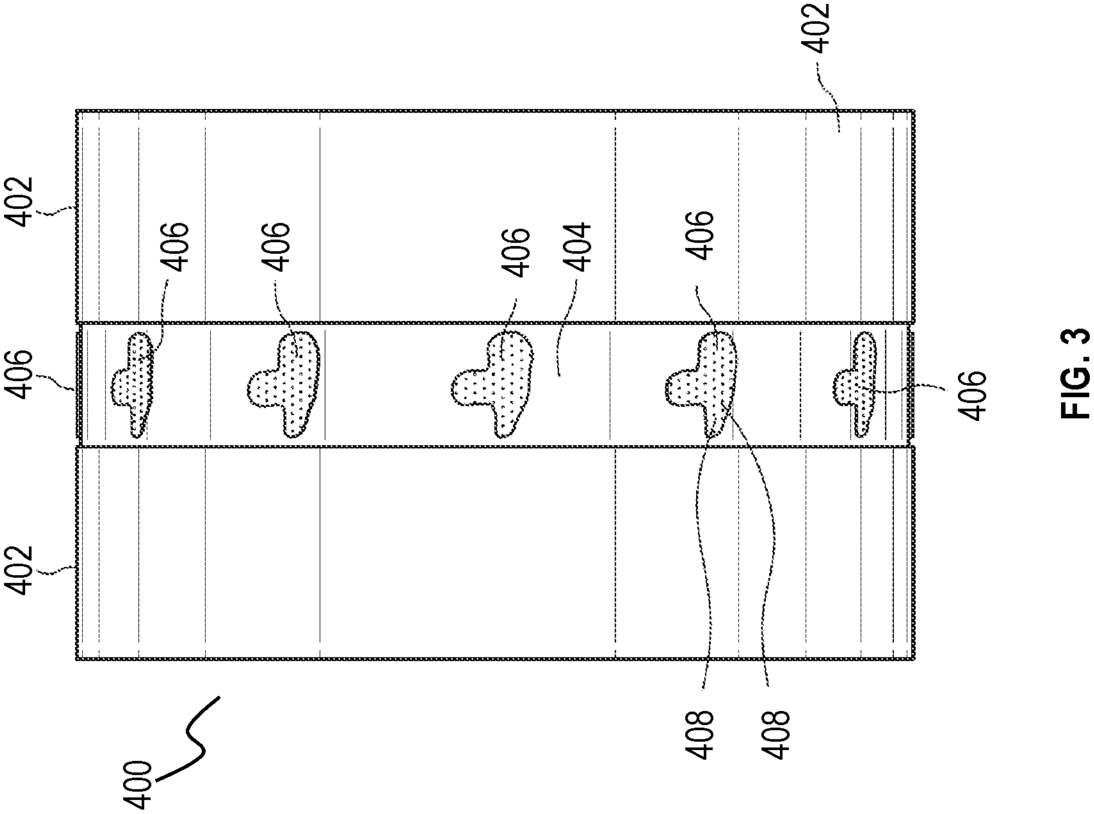
FIG. 3 is an example illustrating a schematic side view of a first device.

FIG. 3 is an example illustrating a schematic side view of a first device 400. The first device 400 may comprise an outer surface 402 and one or more circumferential recessed portions 404. Within the one or more circumferential recessed portions 404, the first device may comprise one or more raised portions 406. Each of the raised portions 406 may comprise a plurality of recesses 408.

Figure 4:
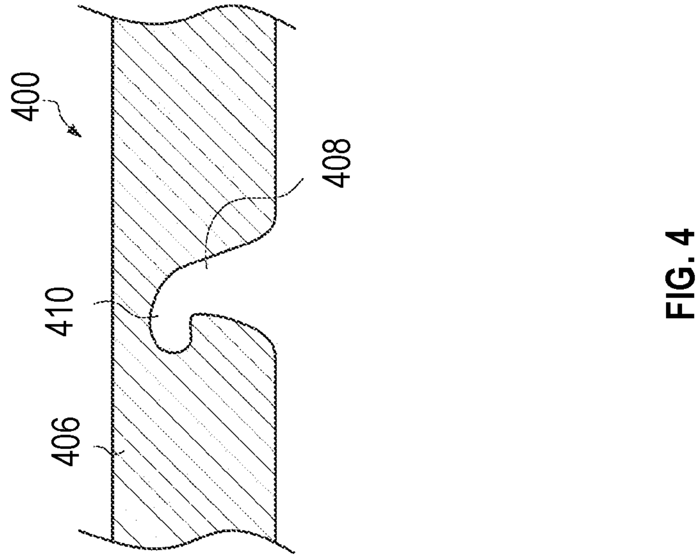
FIG. 4 is an example illustrating a schematic cross-sectional view of a portion of the first device having a shape configured to produce projections or hooks.

FIG. 4 is an example illustrating a schematic cross-sectional view of a recess 408 of a raised portion 406 of the first device 400. The recess 408 may have a shape 410 configured to produce hook-shaped projections, which may be used as a component of a hook-and-loop-type fastener.

Figure 5:
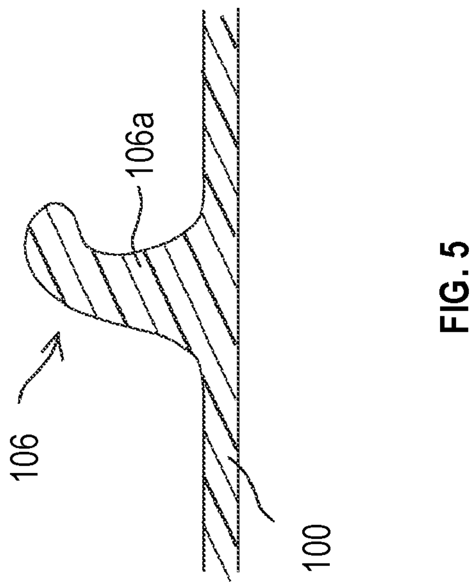
FIG. 5 is an example illustrating a schematic cross-sectional view of a projection or hook fastener.

FIG. 5 is an example illustrating a schematic cross-sectional view of a hook fastener 106 formed in the first substrate 100. The hook fastener 106 may have a hook body **106*a* that extends above a surface of the first substrate 100**.

Figure 6:
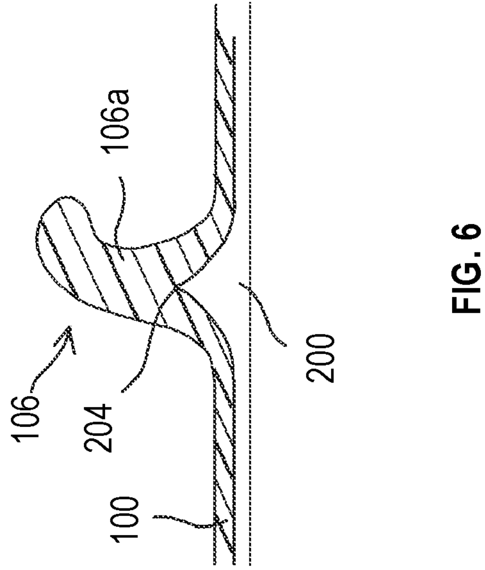
FIG. 6 is an example illustrating a schematic cross-sectional view of a projection or hook fastener.

FIG. 6 is an example illustrating a schematic cross-sectional view of a hook fastener 106 formed in the first substrate 100, as shown in FIG. 5. A second substrate 200 has been joined or bonded to the first substrate 100. A portion 204 of the second substrate may be distributed into the hook body **106*a* as a result of the bonding operation performed in the second nip 46**.

Figure 7:
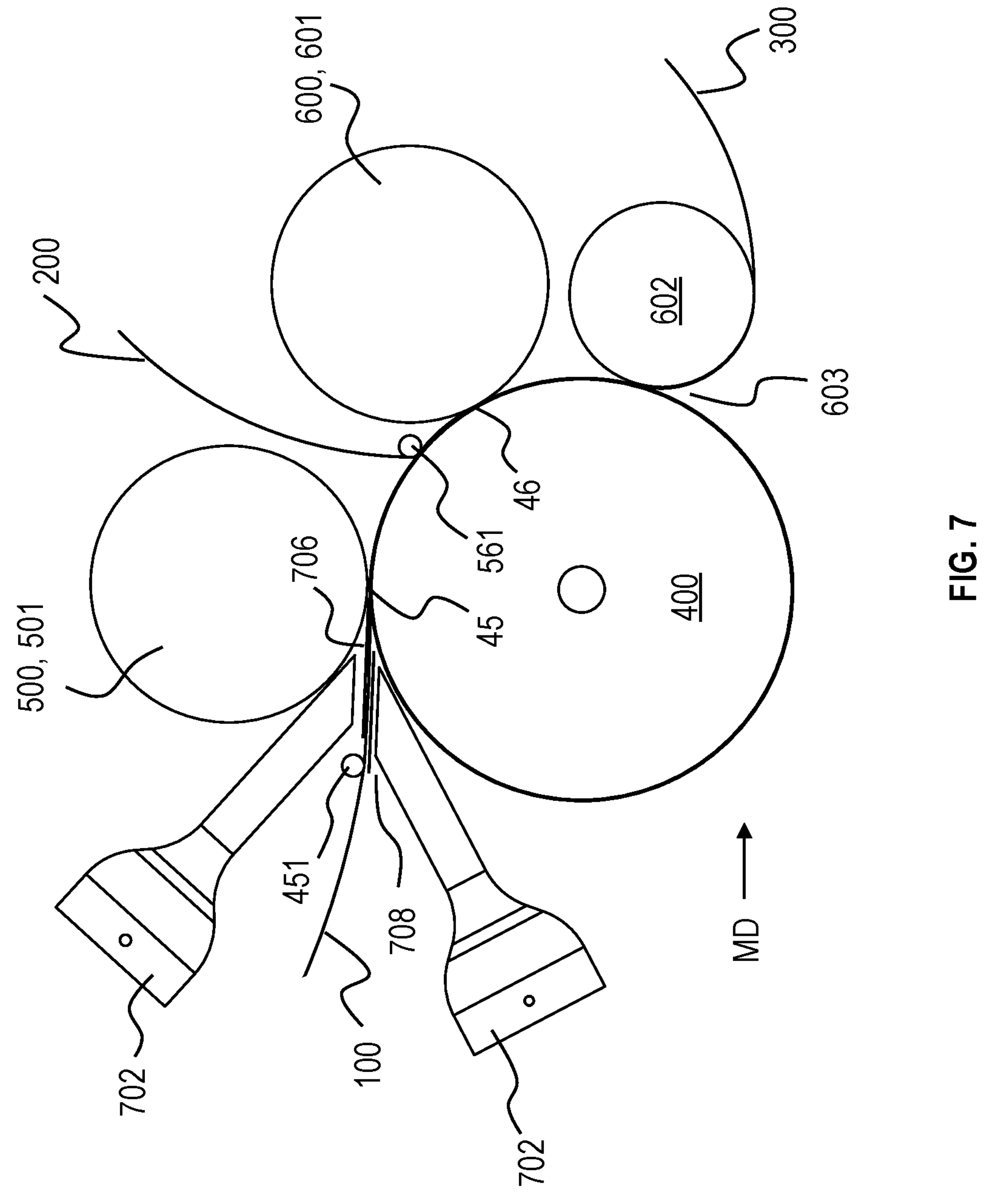
FIG. 7 is an example illustrating a schematic side view of a method and an apparatus for forming a laminate, the method employing and the apparatus including a plurality of sonotrodes each having a web handling device disposed upstream thereof.

FIG. 7 is an example illustrating a schematic side view of a method and an apparatus for forming a laminate 300. The first device 500, comprising a first source of vibration energy 501, may be any type of sonotrode, such as a rotary sonotrode. Similarly, the second device 600, comprising a second source of vibration energy 601, may be any type of sonotrode, such as a rotary sonotrode. A first web handling device 451 may be positioned upstream of the first device 500. A second web handling device 461 may be positioned upstream of the second device 600. The web handling devices 451, 461 may maintain a desired degree of tension on the first substrate 100 and the second substrate 200 as the substrates 100, 200 are conveyed through the first nip 45 and the second nip 46. The web handling devices 451, 461 may be any type of web handling device, including but not limited to a web spreading device, a flat bar, a bar roller, or an idler roll. A flat stationary bar may be preferred according to various configurations to reduce web wrinkles upon heating, which were observed with some idler rolls. Although not illustrated in all of the figures in this disclosure, it is to be appreciated that such web handling devices 451, 461 may be employed in any configuration disclosed herein. The method and apparatus may further comprise one or more preheaters 702. The preheaters 702 may apply heated air to the first substrate 100 before the first substrate 100 enters the first nip 45. An upper heat shield 706 and a lower heat shield 708 may be disposed between the preheaters 702 to deflect the heated air away from portions of the substrate that do not need to be preheated. The first substrate 100 may be conveyed between the upper heat shield 706 and the lower heat shield 708. Similar preheaters may be used to preheat the second substrate 200, as will be illustrated hereinafter. After exiting the second nip 46, the laminate 300 may be passed over a tensioning roller 602, which may help maintain contact between the laminate 300 and the first device 400 to give the hook fastener 106 formed in the first substrate 100 time to cool and set before being removed from the recesses 408 in the first device 400 at an unmolding point 603.

Figure 8:
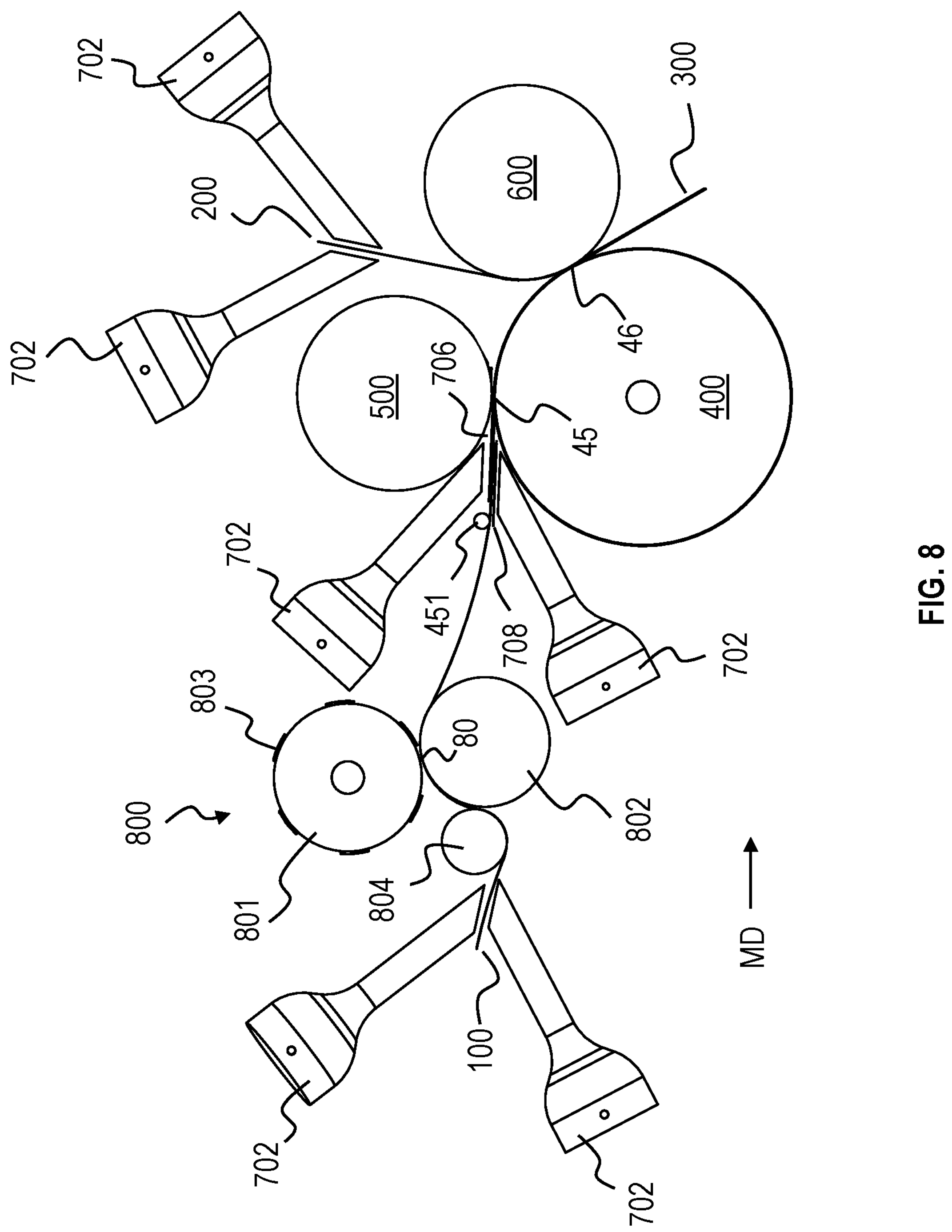
FIG. 8 is an example illustrating a schematic side view of a method and an apparatus for forming a laminate, the method employing and the apparatus including a plurality of preheaters and a flattening roller.
Figure 9:
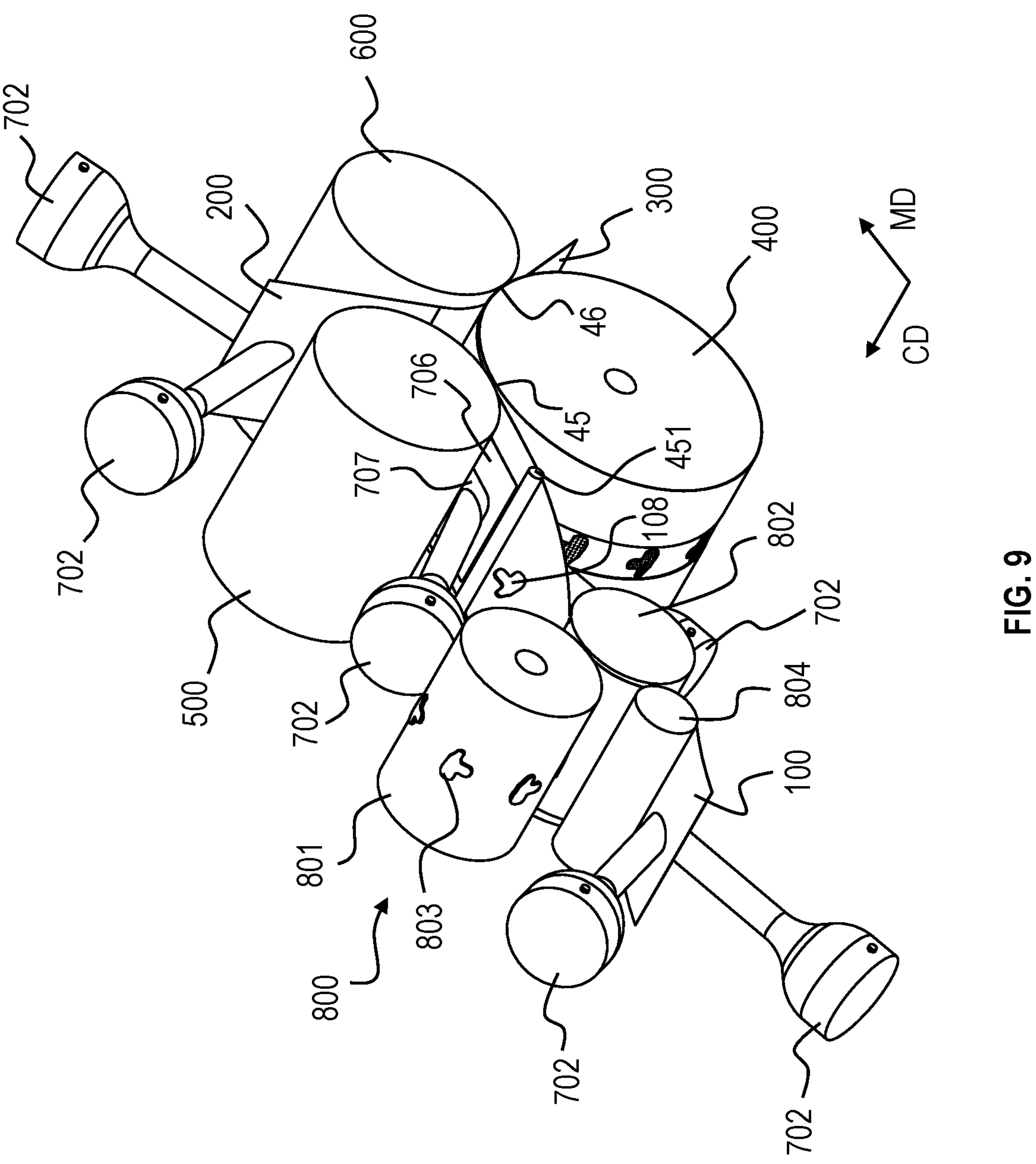
FIG. 9 is an example illustrating a schematic perspective view of the method and the apparatus as shown in FIG. 8.

FIG. 8 is an example illustrating a schematic side view of a method and an apparatus for forming a laminate 300, the method employing and the apparatus including a plurality of preheaters 702 and a flattening roller 800. The flattening apparatus 800 may comprise a first flattening roller 801 and a second flattening roller 802. A third nip 80 may be formed between the first flattening roller 801 and the second flattening roller 802. The first substrate 100 may be conveyed through the third nip 80. The first flattening roller 801 may comprise one or more raised portions 803 that may press the first substrate against the second flattening roller 802 to create flatten portions 108 (see: FIG. 9) of the first substrate 100. The flattening apparatus 800 may optionally include a tensioning roller 804 disposed upstream of the third nip 80 to achieve a desired tension in the first substrate 100 and to ensure good contact between the first substrate 100 and the second flattening roller 802 prior to the third nip 80. One or more preheaters 702 may be disposed upstream of the flattening apparatus 800 in a position to preheat the first substrate 100 before it reaches the third nip 80. One or more preheaters 702 may be disposed upstream of the first nip 45 in a position to preheat the first substrate 100 before it enters the first nip 45. Finally, one or more preheaters 702 may be disposed upstream of the second nip 46 in a position to preheat the second substrate 200.

FIG. 9 is an example illustrating a schematic perspective view of the method and the apparatus as shown in FIG. 8. The raised portions 803 may be disposed periodically around the outer surface of the first flattening roller 801 to create intermittently spaced flattened areas 108 on the first substrate. Also shown in FIG. 9, is an aperture 707 in the upper heat shield 706. The lower heat shield 708 may comprise a similar aperture. The aperture 707 allows heated air from the preheaters 702 to reach the desired portion of the targeted substrate(s).

Figure 10:
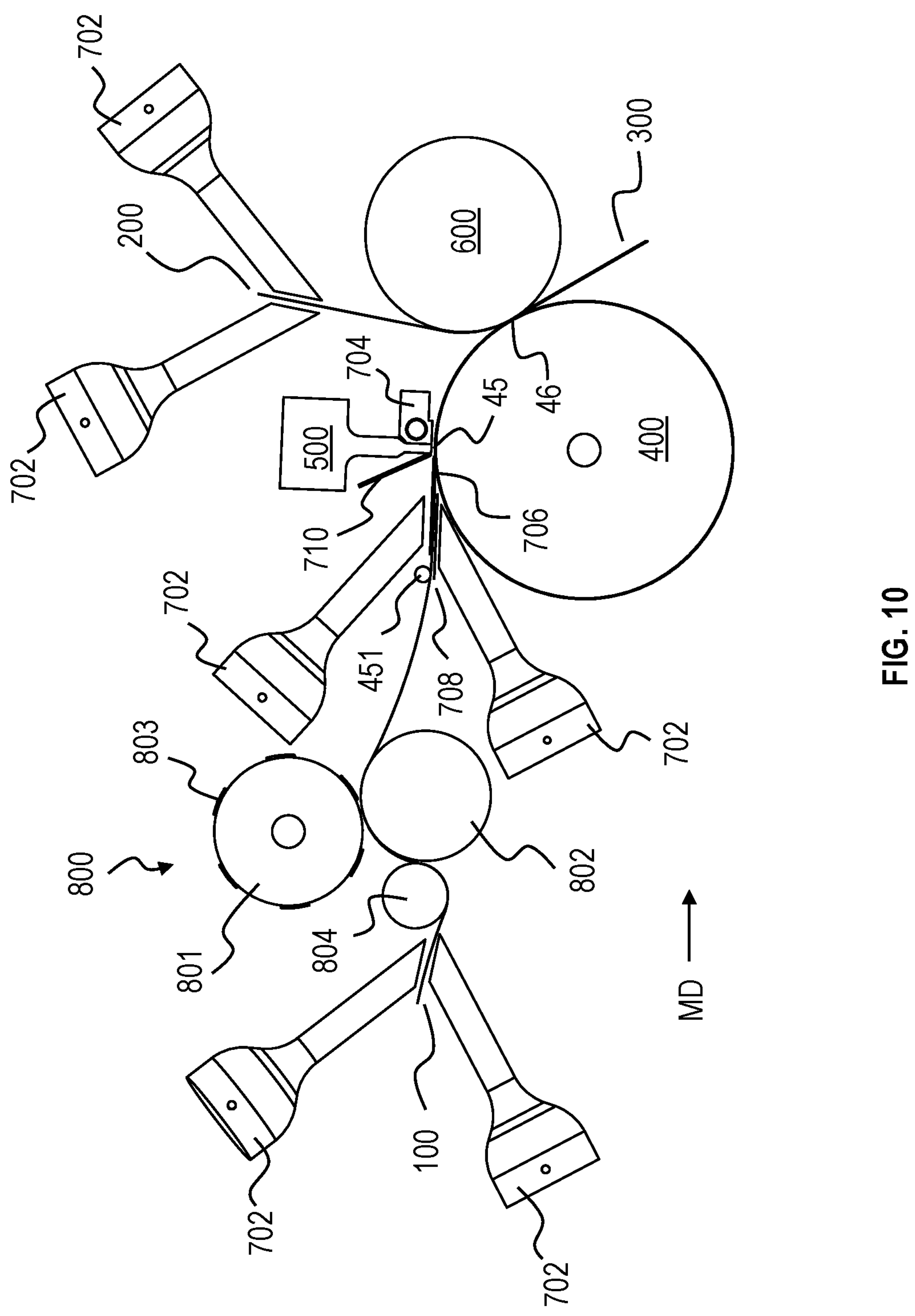
FIG. 10 is an example illustrating a schematic side view of a method and an apparatus for forming a laminate, the method employing and the apparatus including a blade sonotrode and a rotary sonotrode.
Figure 11:
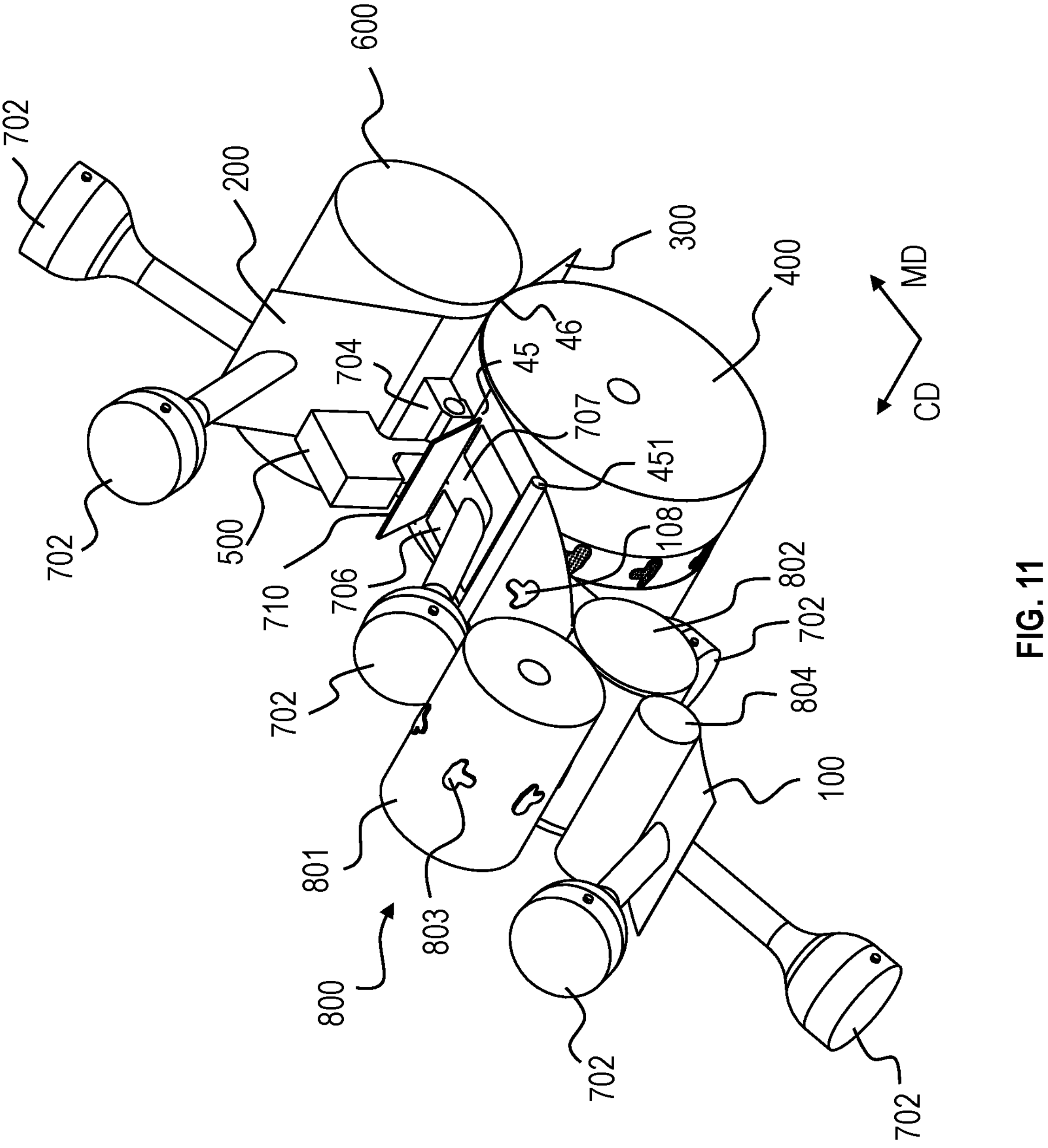
FIG. 11 is an example illustrating a schematic perspective view of the method and the apparatus as shown in FIG. 10.

FIG. 10 is an example illustrating a schematic side view of a method and an apparatus for forming a laminate, the method employing and the apparatus including a blade sonotrode and a rotary sonotrode. FIG. 11 is an example illustrating a schematic perspective view of the method and the apparatus as shown in FIG. 8. As shown in FIG. 10 and FIG. 11, the first device 500 may be a blade sonotrode and the second device 600 may be a rotary sonotrode. The first device 500 may be cooled by a cooling block 704 through which a cooling fluid, such as water, oil, or air may be passed to transfer heat away from the first device 500. An angled heat shield (710) may also be disposed between the first device 500 and the incoming first substrate 100 to reduce heat transfer from the first device 500 to the first substrate 100 prior to the first nip 45 and to block heated air from the preheaters 702 from heating the first device 500.

Figure 12:
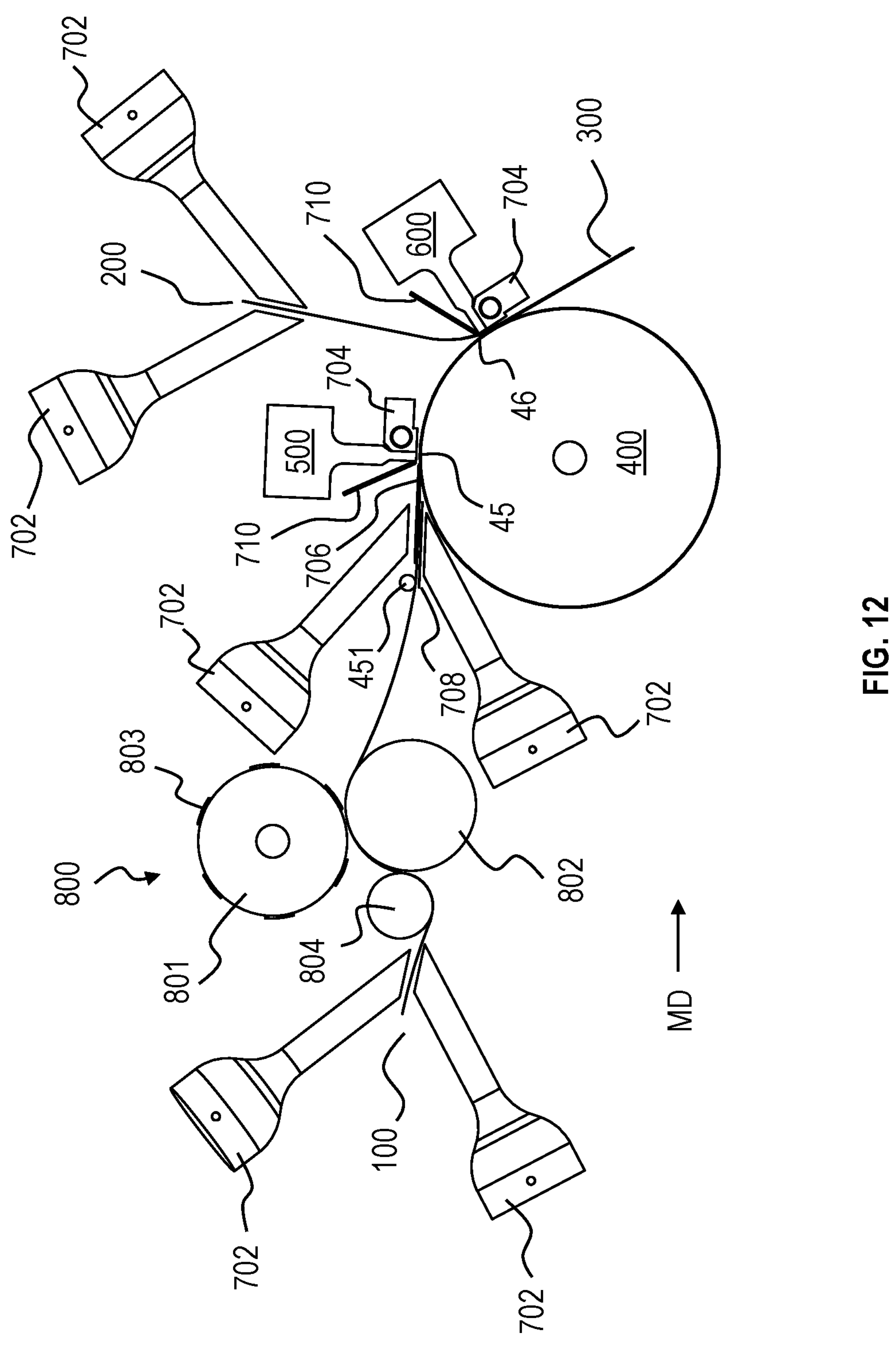
FIG. 12 is an example illustrating a schematic side view of a method and an apparatus for forming a laminate, the method employing and the apparatus including a plurality of blade sonotrodes.

FIG. 12 is an example illustrating a schematic side view of a method and an apparatus for forming a laminate, the method employing and the apparatus including a plurality of blade sonotrodes. Both the first device 500 and the second device 600 may be cooled by a cooling block 704 and both may be shielded by an angled heat shield 710.

Figure 13:
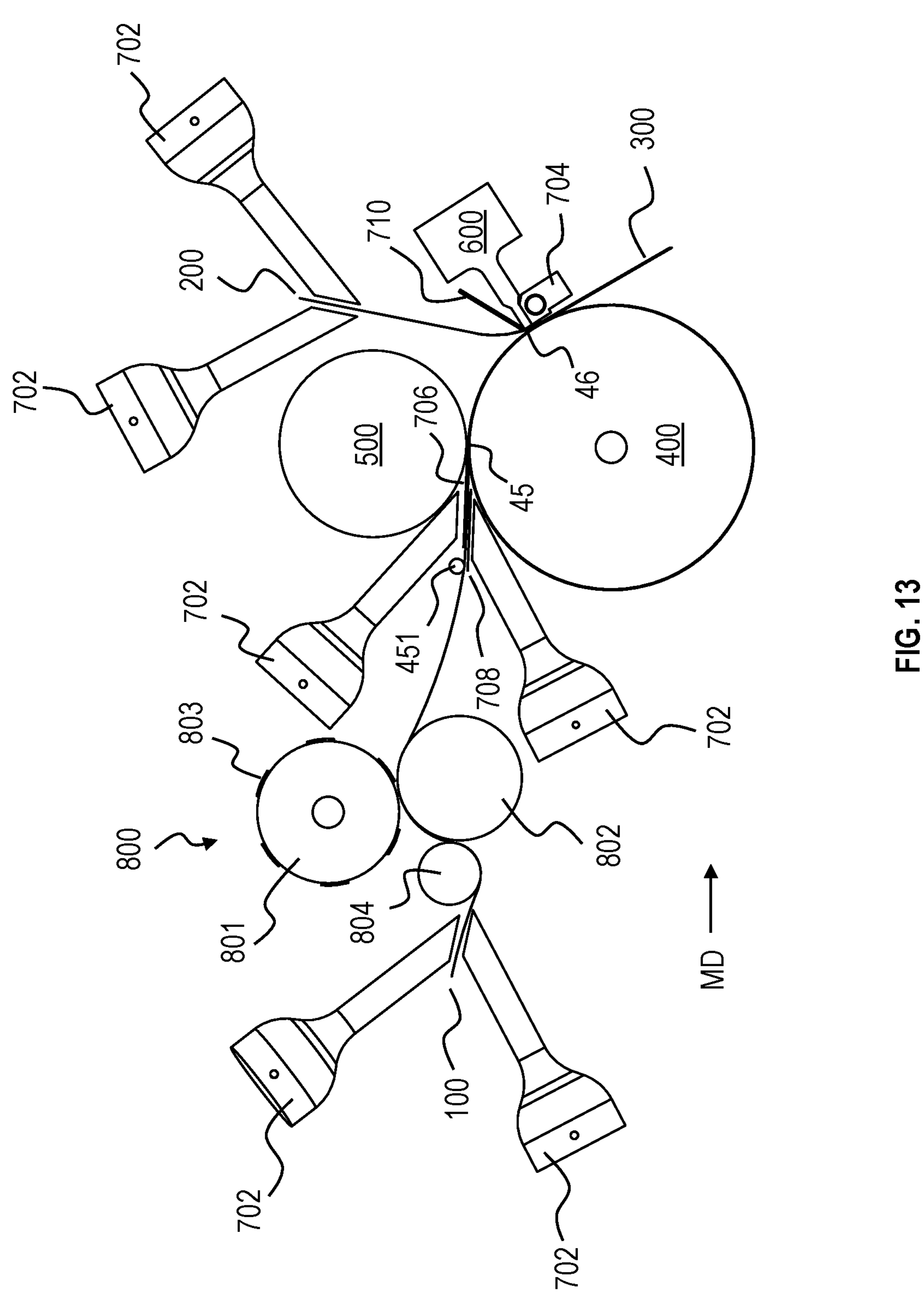
FIG. 13 is an example illustrating a schematic side view of a method and an apparatus for forming a laminate, the method employing and the apparatus including a rotary sonotrode and a blade sonotrode.

FIG. 13 is an example illustrating a schematic side view of a method and an apparatus for forming a laminate, the method employing and the apparatus including a rotary sonotrode and a blade sonotrode. It is to be appreciated that any combination of rotary sonotrodes and blade sonotrodes may be employed.

Figure 14:
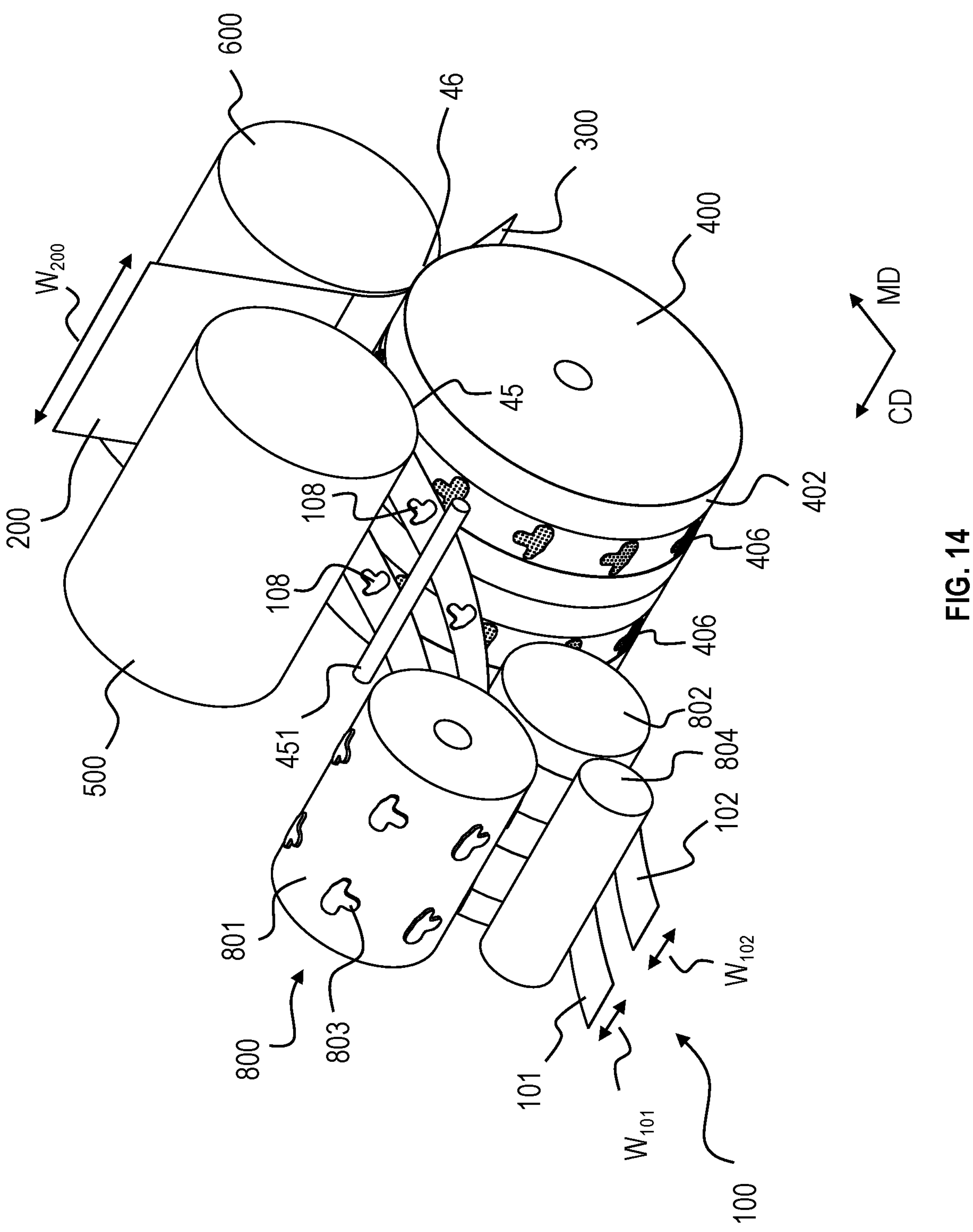
FIG. 14 is an example illustrating a schematic perspective view of a method and an apparatus for forming a laminate from two primary substrates and one secondary substrate, the method employing and the apparatus including a plurality of rotary sonotrodes.
Figure 15:
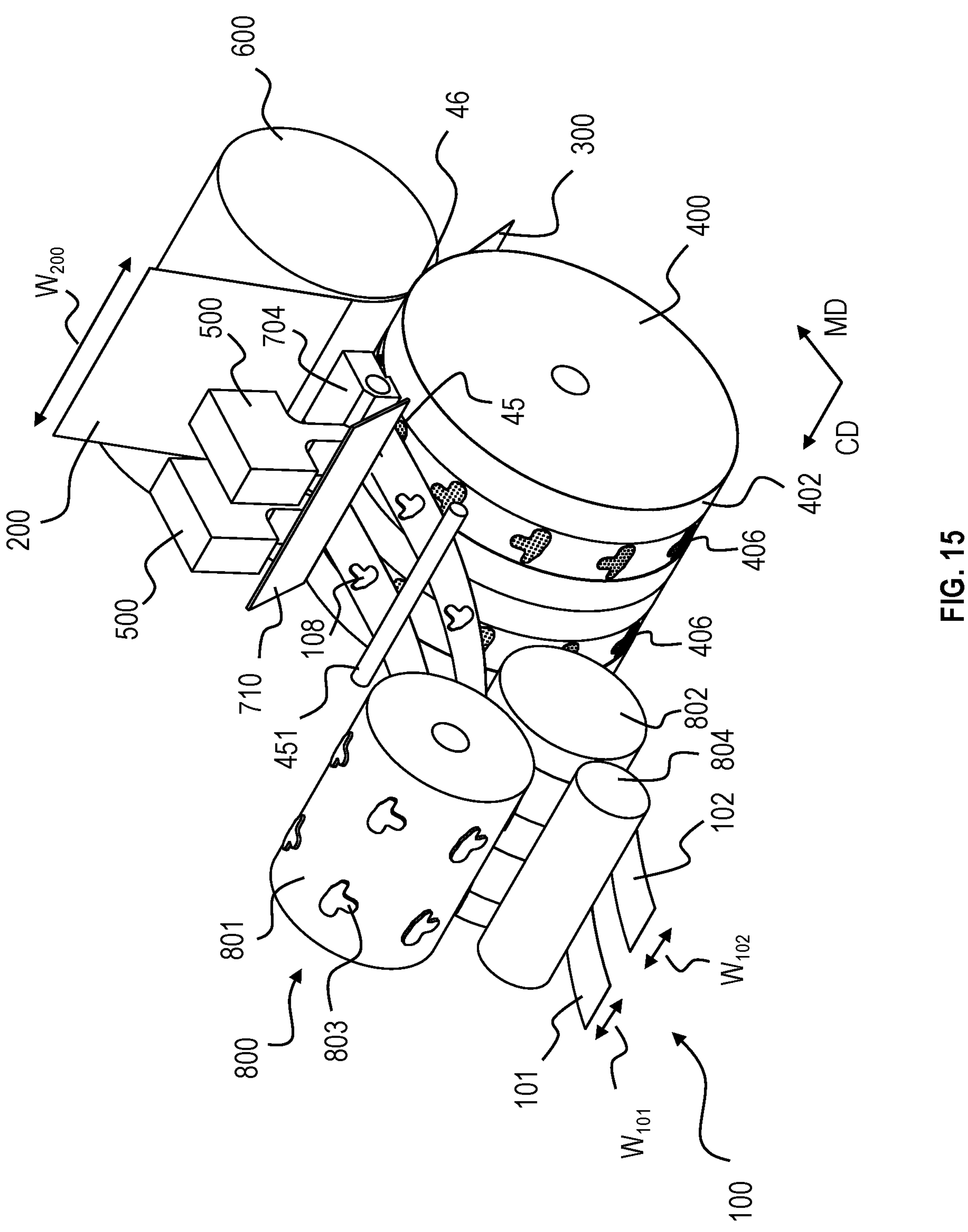
FIG. 15 is an example illustrating a schematic perspective view of a method and an apparatus for forming a laminate from two primary substrates and one secondary substrate, the method employing and the apparatus including a plurality of blade sonotrodes and a rotary sonotrode.
Figure 16:
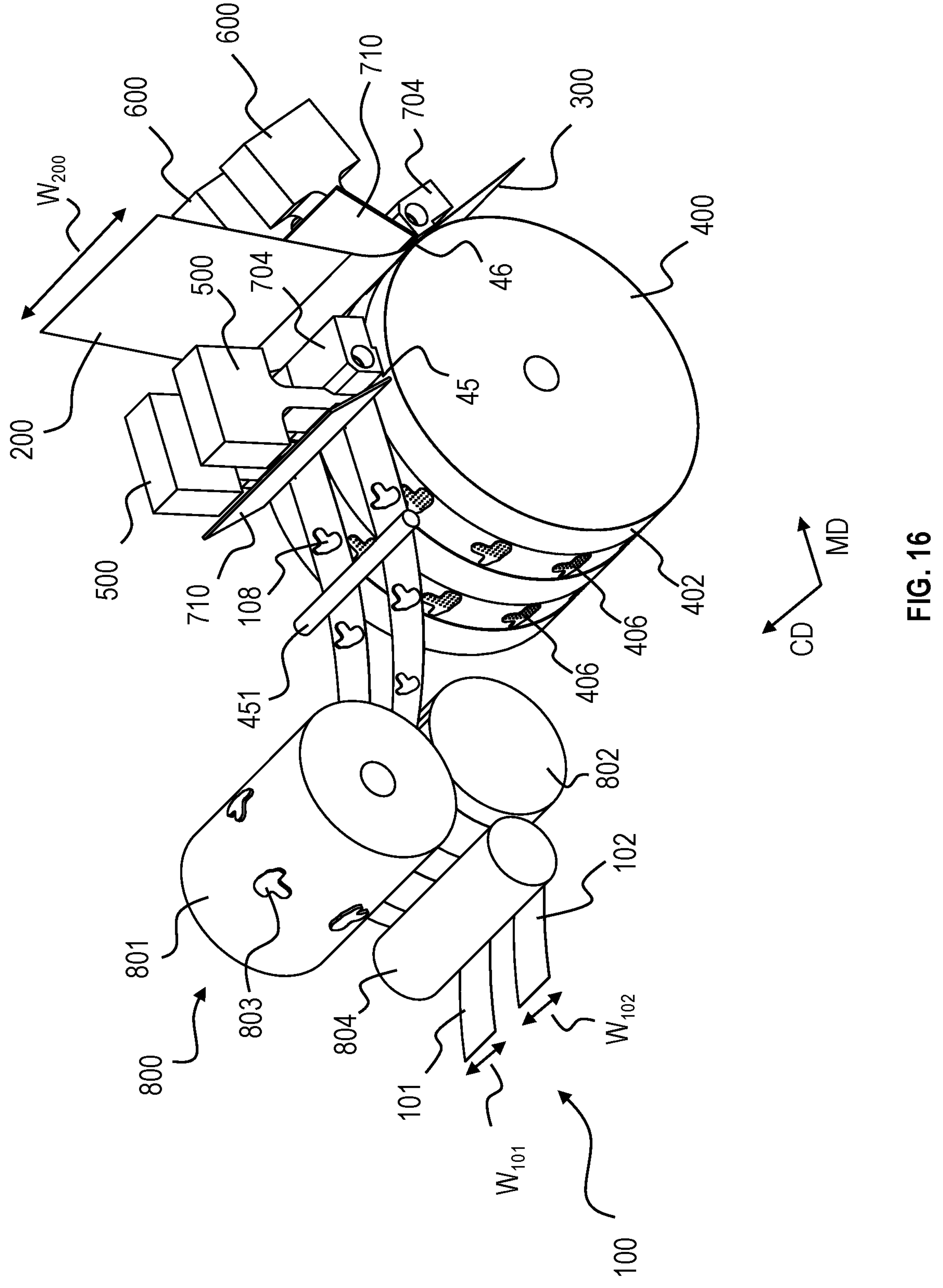
FIG. 16 is an example illustrating a schematic perspective view of a method and an apparatus for forming a laminate from two primary substrates and one secondary substrate, the method employing and the apparatus including a plurality of blade sonotrodes.

FIG. 14, FIG. 15, and FIG. 16 cooperate to illustrate some non-limiting variations of a method and an apparatus for forming a laminate 300 from first substrate 100 comprising a first strip 101 and a second strip 102 and from a second substrate 200. To provide views of the various substrates the method and apparatus has been simplified, but it is to be appreciated that any or all of the elements described in other embodiments may be incorporated. FIG. 14 shows the method employing and the apparatus including a plurality of rotary sonotrodes. FIG. 15 shows the method employing and the apparatus including a plurality of blade sonotrodes and a rotary sonotrode. FIG. 16 shows the method and the apparatus employing a plurality of blade sonotrodes. It is to be appreciated that any combination of rotary sonotrodes and blade sonotrodes may be employed. The first substrate 100 may comprise a plurality of strips. For example, the first substrate 100 may comprise a first strip 101 and a second strip 102. The first strip may have a width $W_{101}$ and the second strip may have a width $W_{102}$. Any number of strips may be employed. The flattening apparatus 800 may include multiple rows or lanes of raised portions 803 to facilitate the creation of flattened areas 108 on each of the plurality of strips. Similarly, the first device 400 may include multiple rows or lanes of raised portions 406 on its outer surface 402 to facilitate the creation of intermittent altered areas 104 on each of the plurality of strips, which as previously described may comprise protrusions or hooks 106. According to various configurations, the width $W_{200}$ second substrate 200 may be greater than the sum of the widths of the plurality of strips. For example, the width $W_{200}$ of the second substrate 200 may be greater than the sum of the width $W_{101}$ of the first strip 101 and the width $W_{102}$ of the second strip 102. As shown in FIG. 6, the second substrate 200 may be bonded to each of the plurality of strips 101, 102 directly over the altered areas 104 of the strips, where the protrusions or hooks 106 have been formed. Additionally or alternatively, and as will be discussed in greater detail hereinafter with respect to FIGS. 21 and 24, the second substrate 200 may be bonded to the plurality of strips 101, 102 between the altered areas 104, i.e., in unformed areas 110 of the strips 101, 102.

Figure 17:
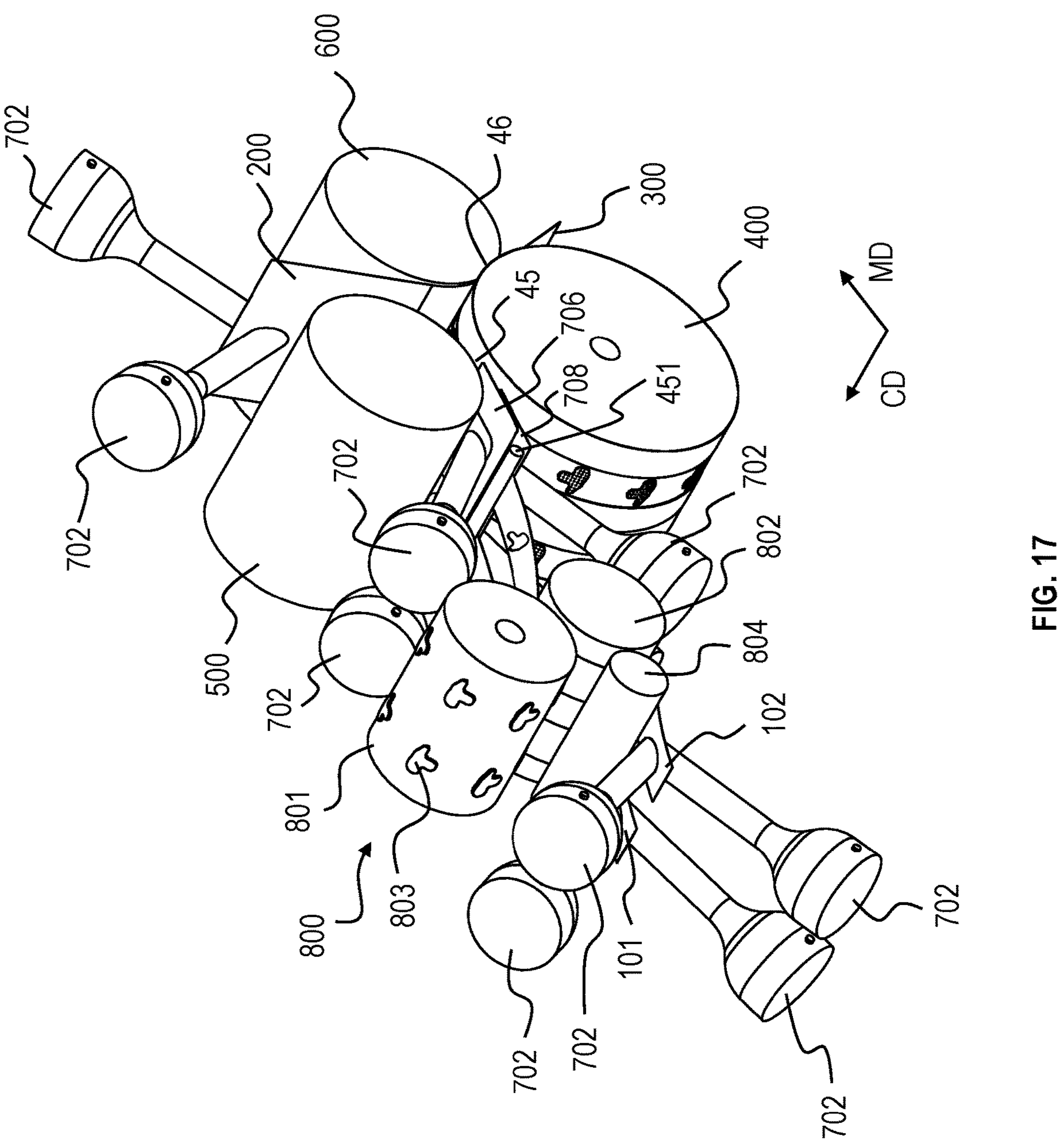
FIG. 17 is an example illustrating a schematic perspective view of a method and an apparatus for forming a laminate from two primary substrates and one secondary substrate, the method employing a plurality of preheaters and a flattening roller.

FIG. 17 is an example illustrating a schematic perspective view of a method and an apparatus for forming a laminate from two primary substrates and one secondary substrate, the method employing a plurality of preheaters 702 and a flattening apparatus 800. As shown, each the plurality of strips 101, 102 may be heated with one or more preheaters 702 both upstream of the flattening apparatus 800 and upstream of the first nip 45. The upper heat shield 706 and the lower heat shield 708 may include a plurality of apertures 707 to allow warm air from the plurality of preheaters 702 to reach the plurality of strips 101, 102.

Figure 18:
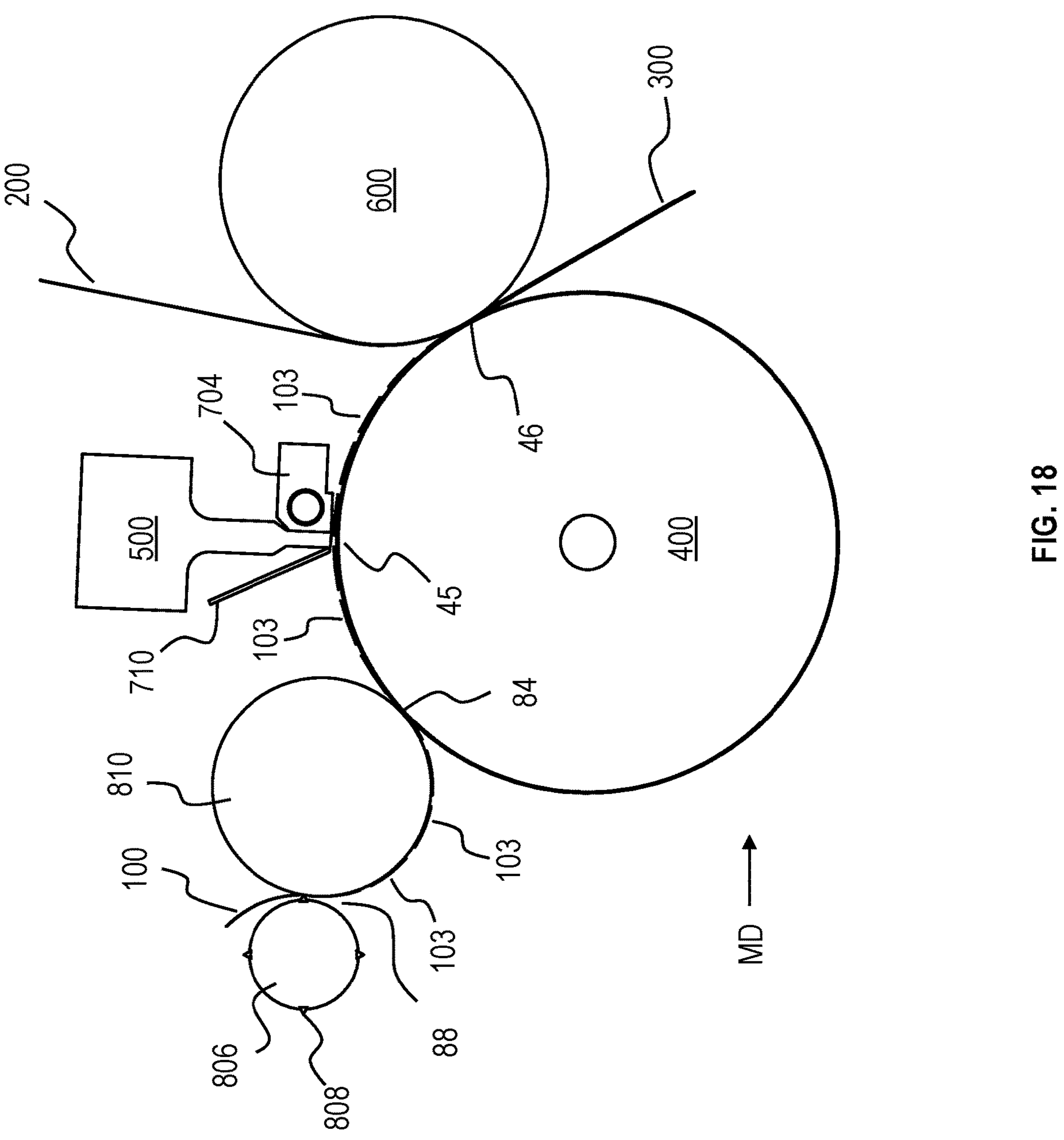
FIG. 18 is an example illustrating a schematic side view of a method and an apparatus for forming a laminate from a plurality of discrete substrate pieces.
Figure 19:
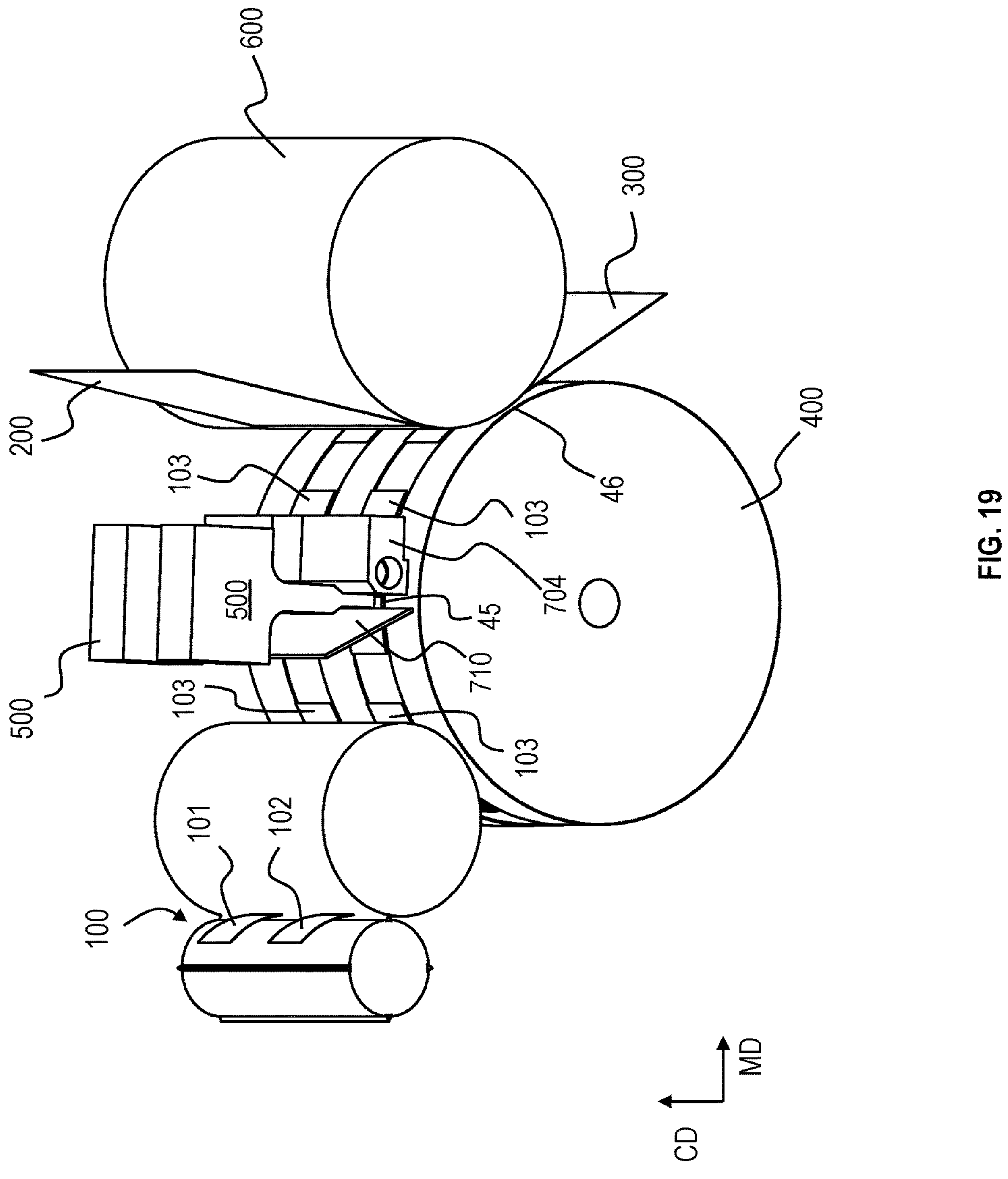
FIG. 19 is an example illustrating a schematic perspective view of the method and the apparatus as shown in FIG. 18.
Figure 20:
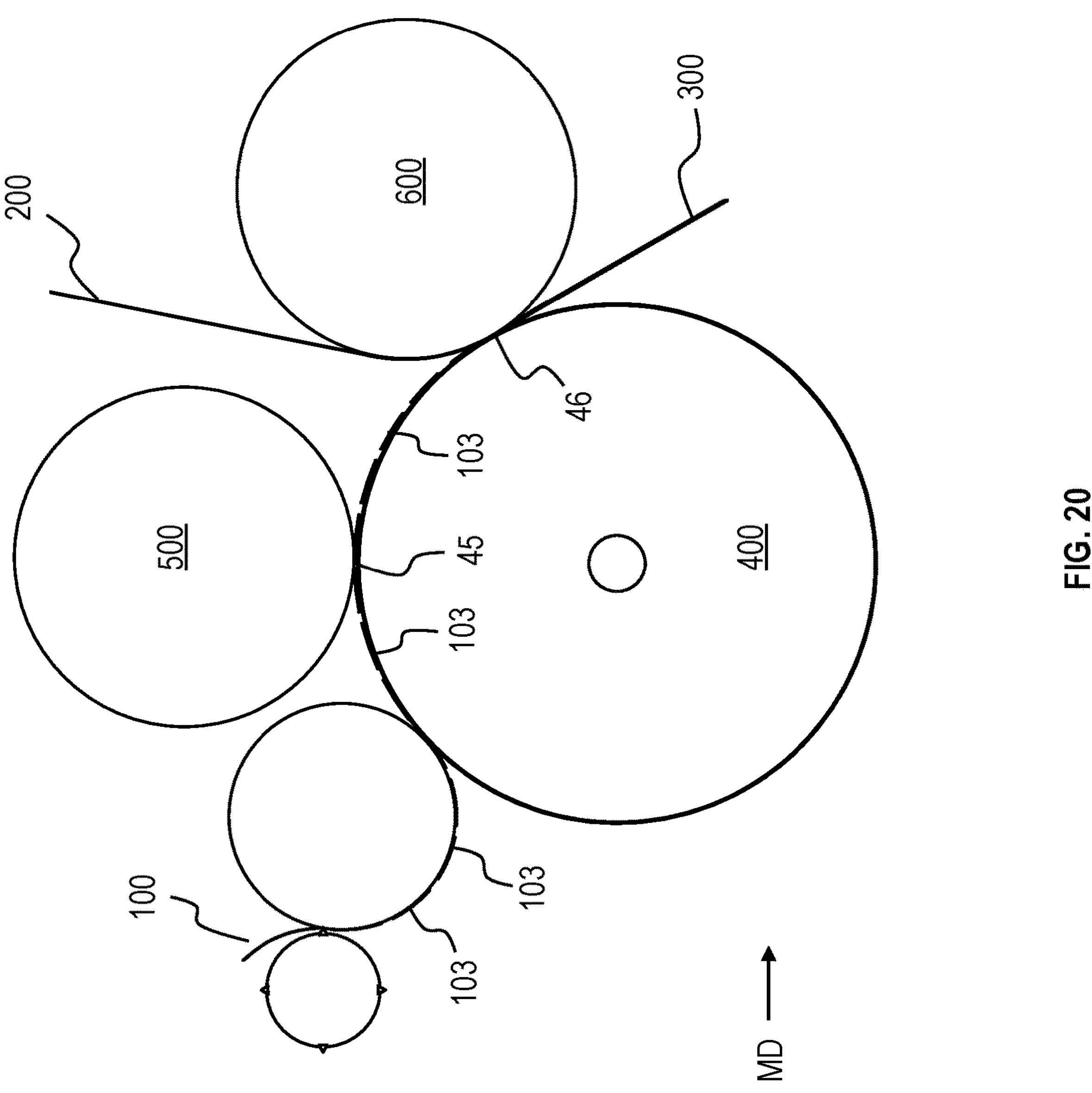
FIG. 20 is an example illustrating a schematic side view of the method and the apparatus as shown in FIG. 18, but with the method employing and the apparatus including a plurality of rotary sonotrodes.

FIG. 18 is an example illustrating a schematic side view of a method and an apparatus for forming a laminate 300 from a plurality of discrete substrate pieces 103. FIG. 19 is an example illustrating a schematic perspective view of the method and the apparatus as shown in FIG. 18. FIG. 20 is an example illustrating a schematic side view of the method and the apparatus as shown in FIG. 18, but with the method employing and the apparatus including a plurality of rotary sonotrodes. It is to be appreciated that any combination of rotary sonotrodes and blade sonotrodes may be employed. As shown the method and apparatus according to various configurations may comprise a cutting roller 806 having one or more blades 808. A fourth nip 88 may be formed between the cutting roller 806 and a vacuum-assisted roller 810. As the first substrate 100 is conveyed through the fourth nip 88, the first substrate 100 may be cut into a plurality of discrete pieces 103. The plurality of discrete pieces may each be held to the outside surface of the vacuum-assisted roller 810 via a vacuum force supplied by a vacuum means (not shown). A fifth nip 84 may be formed between the vacuum-assisted roller 810 and the outside surface 402 of the first device 400. The first device 400 may also be vacuum-assisted meaning that a vacuum force supplied by a vacuum means (not shown) may suction the discrete pieces 103 to the outer surface 402 of the first device 400. The plurality of discrete pieces 103 may then be conveyed through the first nip 45 where they may be altered to form protrusions or hooks 106. The altered pieces 103 may then be passed through the second nip 46 to be bonded to the second substrate 200 to form a laminate 300. It is also to be appreciated that although not shown to simplify the figures, any or all of the components described herein may be employed, including but not limited to a flattening apparatus 800, preheaters 702, web handling devices 451, 561, etc. The flattening apparatus 800, for example, may be positioned upstream or downstream of the cutting roller 806.

New Fig. illustrating that the second substrate may comprise a plurality of strips.

Figures 21, 22:
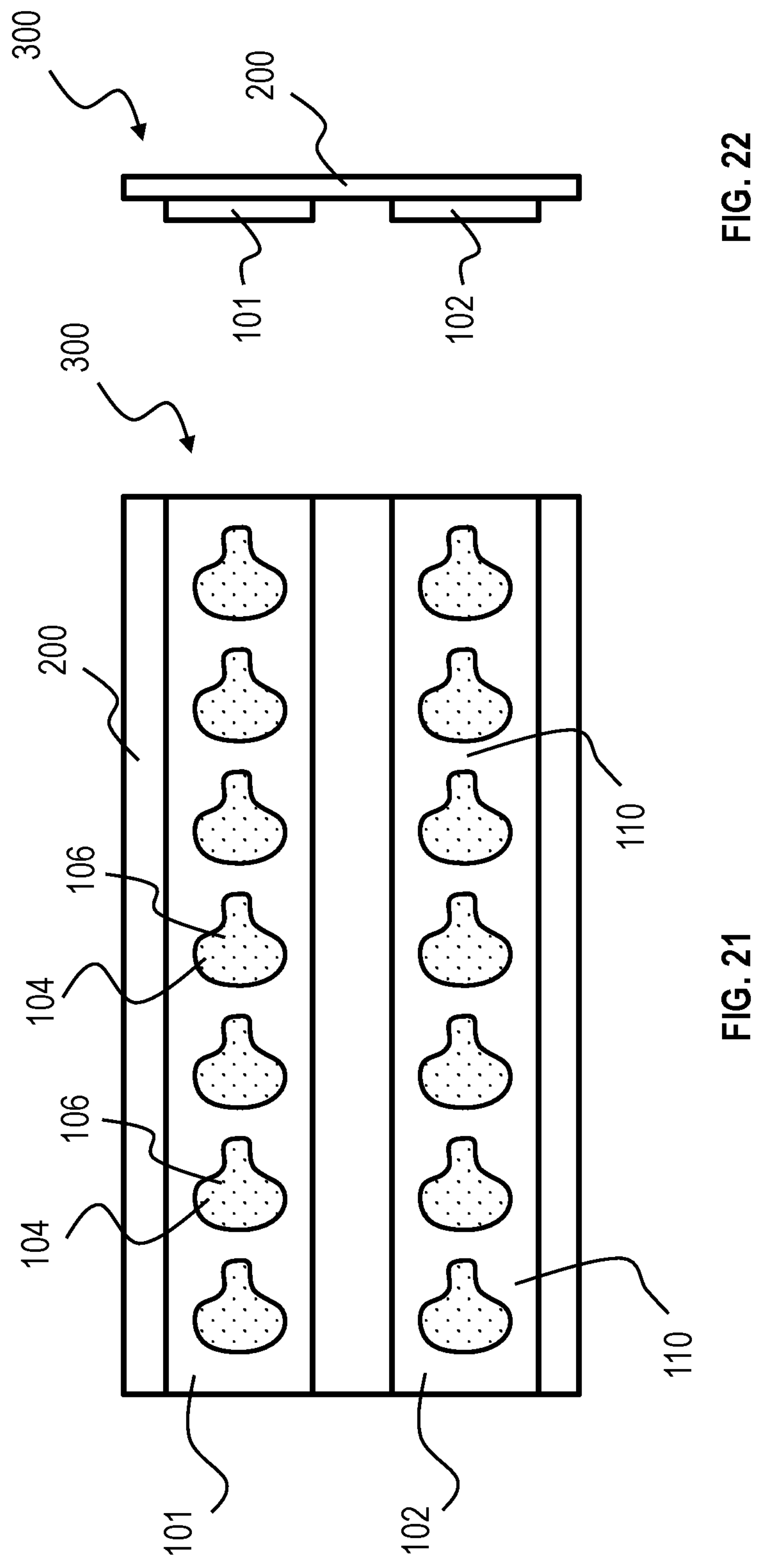
FIG. 21 is an example illustrating a schematic top view of a laminated substrate comprising a plurality of substrates, some having altered portions.
FIG. 22 is an example illustrating a schematic side view of the laminated substrate as shown in FIG. 21.

FIG. 21 is an example illustrating a schematic top view of a laminated substrate comprising a plurality of substrates, some having altered portions. FIG. 22 is an example illustrating a schematic side view of the laminated substrate as shown in FIG. 21. More specifically, the laminate 300 comprises a first strip 101 and a second strip 102 bonded to a second substrate 200. The first strip 101 and the second strip 102 may comprise a plurality of altered areas 104, which may be intermittently spaced along a surface thereof. The altered areas 104 may comprise a plurality of protrusions or hooks 106 suitable for forming a touch fastener. The first strip 101 and the second strip 102 may comprise a plurality of unaltered or unformed areas 110 disposed between and/or around the altered areas 104.

Figures 23, 24:
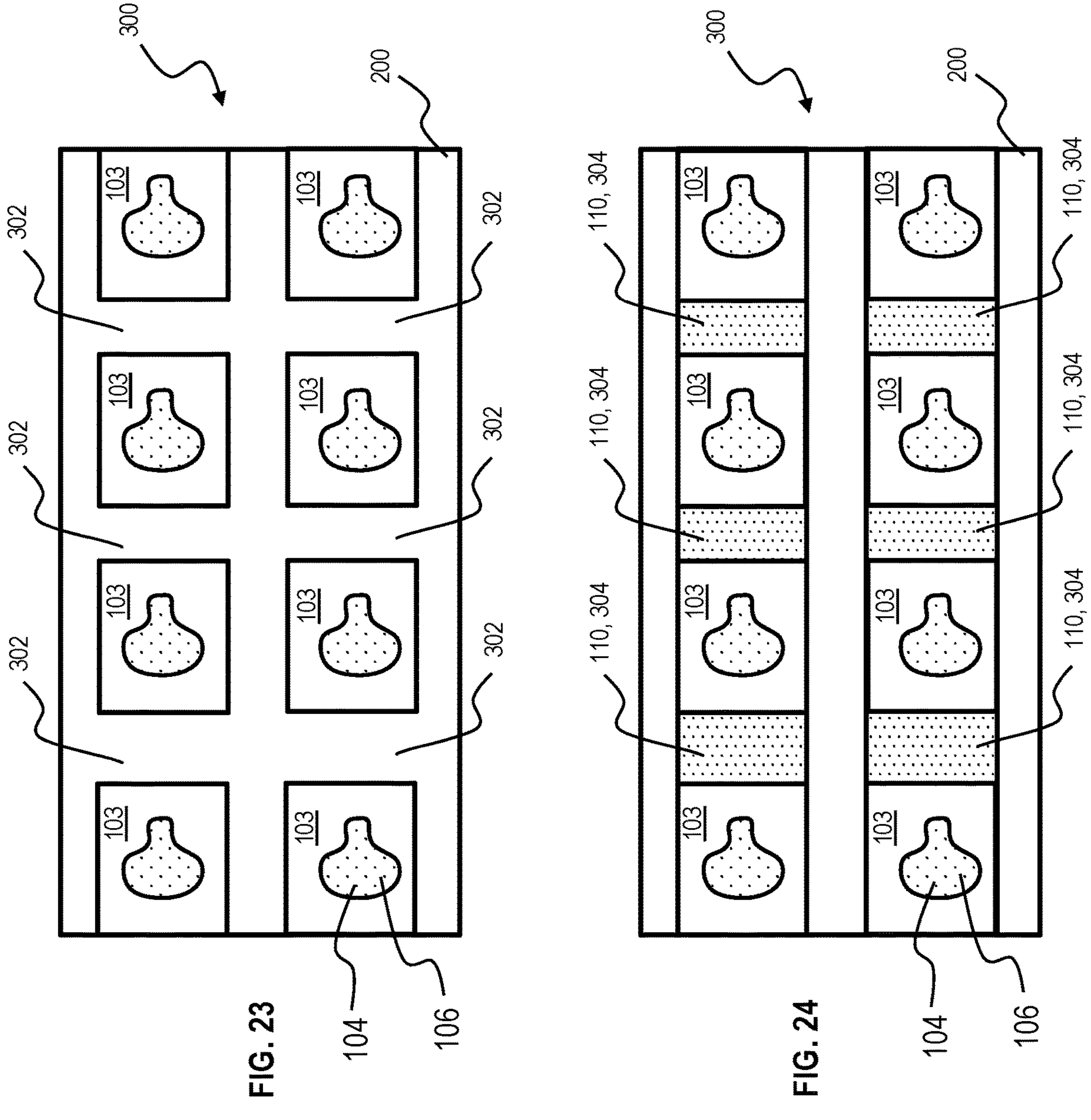
FIG. 23 is an example illustrating a schematic top view of a laminated substrate comprising a plurality of substrates, some having altered portions.
FIG. 24 is an example illustrating a schematic top view of a laminated substrate comprising a plurality of substrates, some having altered portions, the laminated substrate having bond sites only between the altered portions.

FIG. 23 is an example illustrating a schematic top view of a laminated substrate comprising a plurality of substrates, some having altered portions. More specifically, the laminate 300 comprises a plurality of discrete pieces 103. Some or all of the discrete pieces 103 may comprise an altered area 104 comprising a plurality of protrusions or hooks 106 suitable for forming a touch fastener. The discrete pieces 103 may be bonded to a second substrate 200 to form the laminate 300, which may have unaltered areas 302 between and/or around the discrete pieces 103.

FIG. 24 is an example illustrating a schematic top view of a laminated substrate comprising a plurality of substrates, some having altered portions, the laminated substrate having bond sites only between the altered portions. More specifically, the first strip 101 and/or the second strip 102 may be bonded to the second substrate 200, via bonds 304 in unaltered or unformed areas 110 disposed between and/or around the altered areas 104, as illustrated in FIG. 22.

Figure 25:
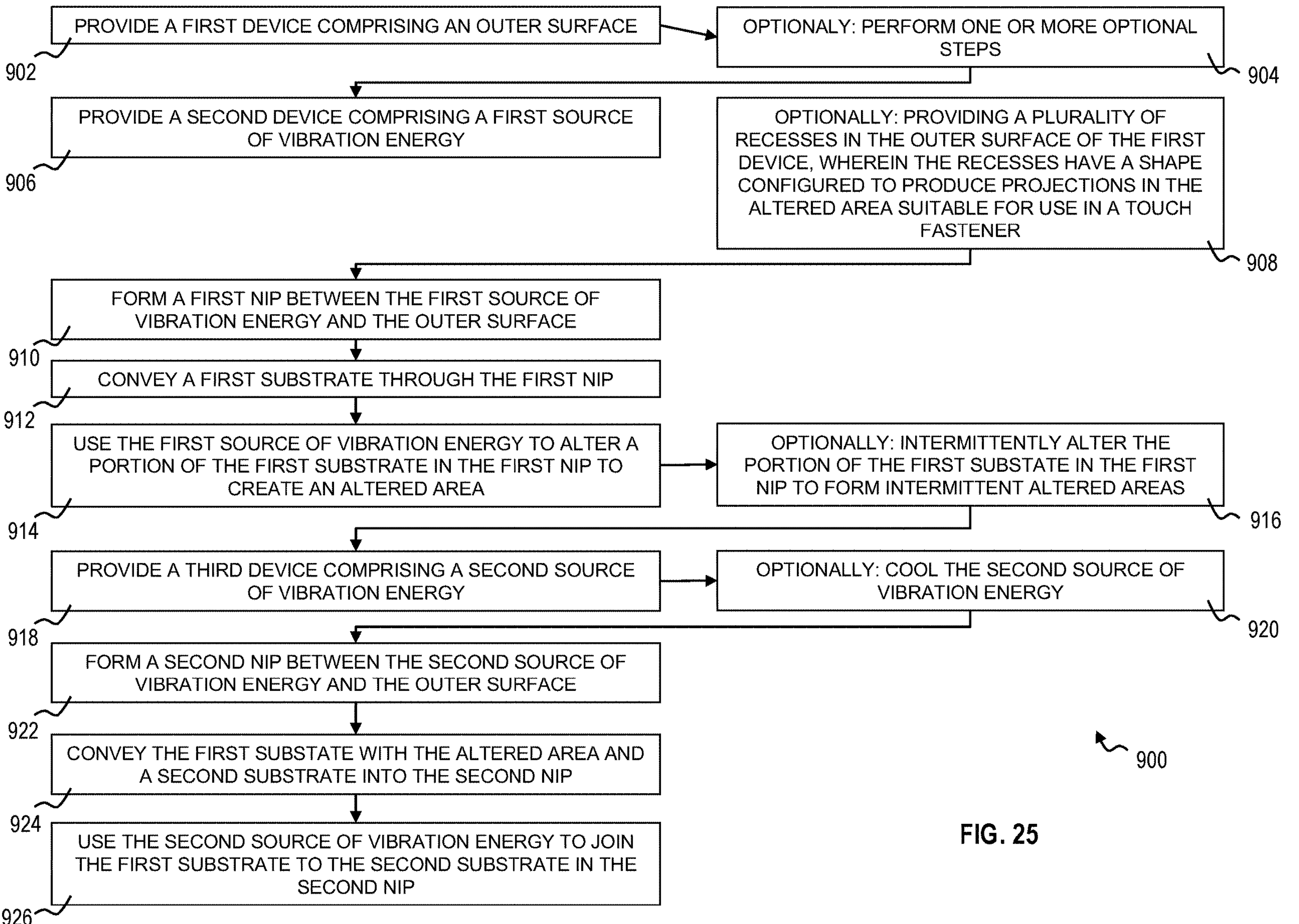
FIG. 25 is an example illustrating a schematic block flow diagram of a method of forming a laminate.

FIG. 25 is an example illustrating a schematic block flow diagram of a method 900 of forming a laminate 300. It is to be appreciated that the order of the steps may be rearranged, reconfigured, and repeated as desired. At step 902, the method 900 may comprise providing a first device 400 comprising an outer surface 402. At optional step 904, the method 900 may comprise one or more optional steps that are detailed in FIG. 26. At step 906, the method 900 may comprise providing a second device 500 comprising a first source of vibration energy 501. At optional step 908, the method 900 may comprise providing a plurality of recesses 408 in the outer surface 402 of the first device 400, wherein the recesses 408 have a shape 410 configured to produce projections 106 in an altered area 104 suitable for use in a touch fastener. At step 910, the method 900 may comprise forming a first nip 45 between the first source of vibration energy 501 and the outer surface 402 of the first device 400. At step 912, the method 900 may comprise conveying a first substrate 100 through the first nip 45. At step 914, the method 900 may comprise using the first source of vibration energy 501 to alter a portion of the first substrate 100 in the first nip 45 to create an altered area 104. At optional step 916, the method 900 may comprise intermittently altering the portion of the first substrate 100 in the first nip 45 to form intermittent altered areas 104, which may be spaced apart on the first substrate 100. At step 918, the method 900 may comprise providing a third device 600 comprising a second source of vibration energy 601. At optional step 920, the method 900 may comprise cooling the second source of vibration energy 601, for example, via a cooling block 704. At step 922, the method 900 may comprise forming a second nip 46 between the second source of vibration energy 601 and the outer surface 402 of the first device 400. At step 924, the method 900 may comprise conveying the first substrate 100 with the altered area 104 and a second substrate 200 into the second nip 46. At step 926, the method 900 may comprise using the second source of vibration energy 601 to join the first substrate 100 to the second substrate 200 in the second nip 46 to form a laminate 300.

Figure 26:
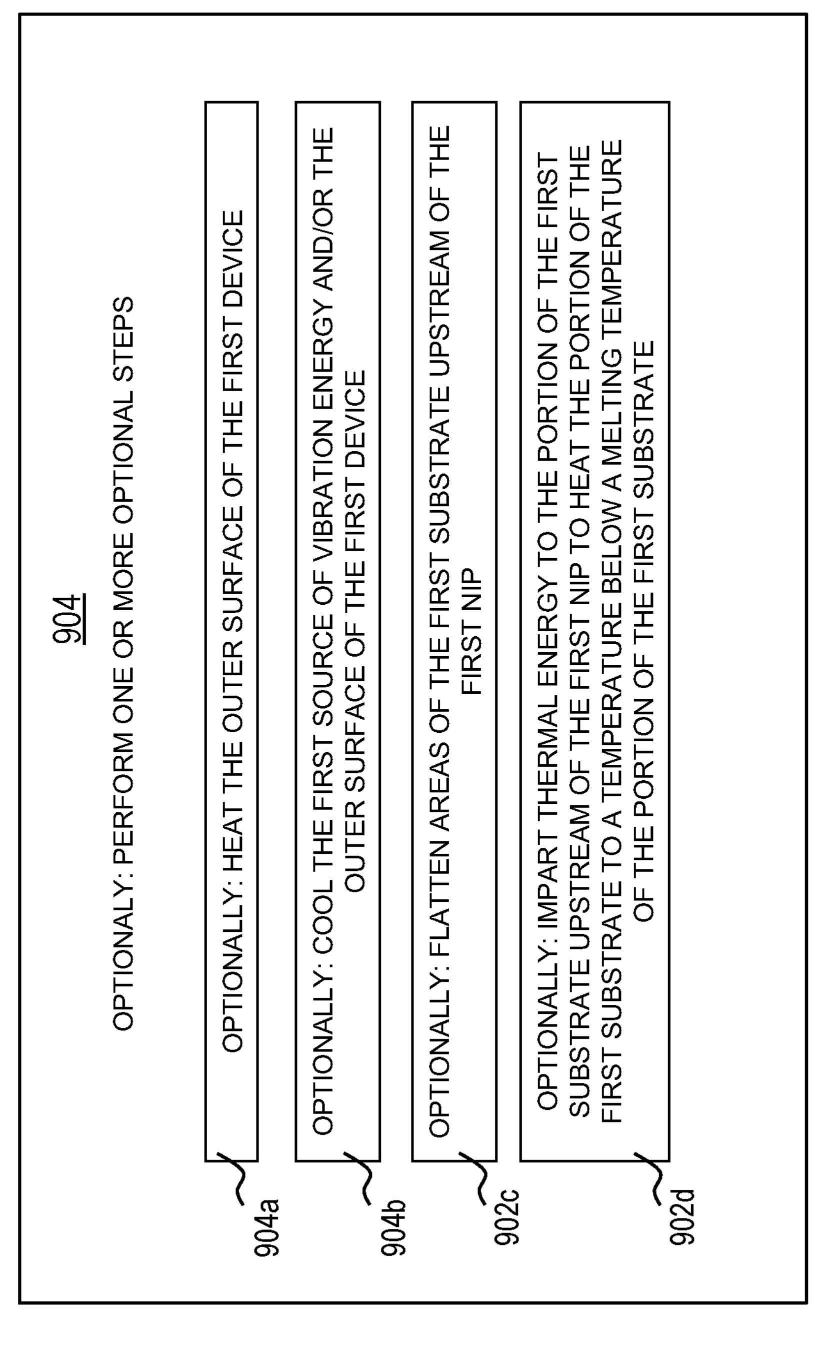
FIG. 26 is an example illustrating a schematic block flow diagram of a detail of some optional steps that may be employed in the method of forming a laminate as illustrated in FIG. 25.

FIG. 26 is an example illustrating a schematic block flow diagram of a detail of some optional steps that may be employed in the method of forming a laminate 300 as illustrated in FIG. 25. Optional step 904 may comprise a step 904*a* of heating the outer surface 402 of the first device 400. Optional step 904 may comprise a step 904*b* of cooling the first source of vibration energy 401 and/or the outer surface 402 of the first device 400. Optional step 904 may comprise a step 904*c* of flatting areas of the first substrate upstream of the first nip 45. Optional step 904 may comprise a step 904*d* of imparting thermal energy to the portion of the first substrate 100 upstream of the first nip 45 to heat the portion of the first substrate 100 to a temperature below a melting temperature of the portion of the first substrate 100.

Figure 27:
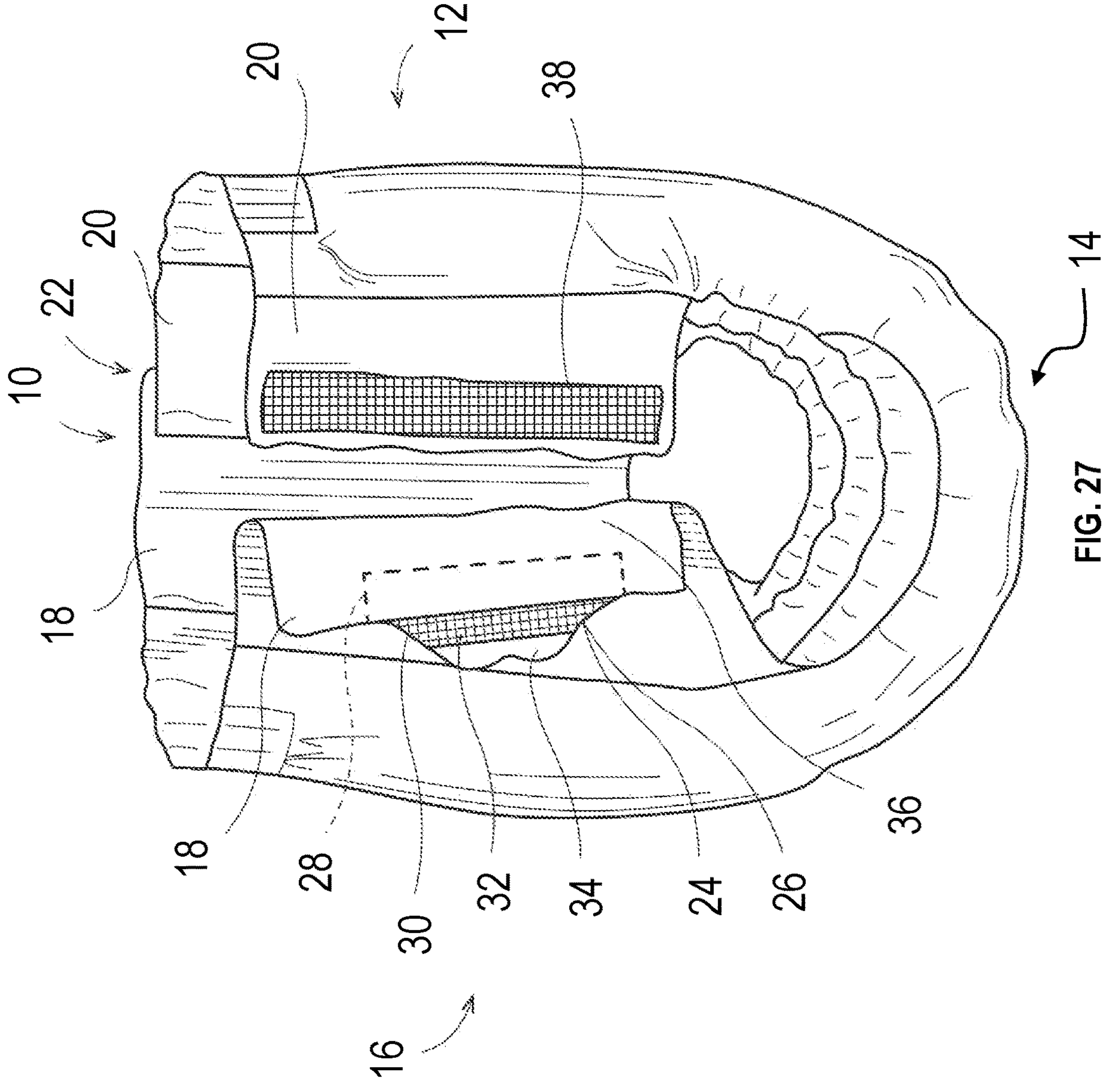
FIG. 27 a side perspective view of an absorbent article with a disposal fastener that is a disposal tab in an unfastened condition.

FIG. 27 a side perspective of the absorbent article 10 wherein the disposal fastener 24 is a disposal tab 26 in an unfastened condition. The disposal fastener 26 may also be used as part of the primary fastening system. The absorbent article 10 may comprise back ears 18 extending from the back waist region 16 and comprise laterally opposite back joining portions 36 (also referred to herein as a first joining portion or a third joining portion). Absorbent article 10 may also comprise front ears 20 extending from front waist region and comprise laterally opposite front joining portions 38 (sometimes referred to as a second joining portion or a fourth joining portion). The back joining portions 36 may be configured for refastenable engagement to corresponding front joining portions 38. Back joining portion 36 of back ear 18 may be joined to front joining portion 38 of front ear 20 to form a refastenable side seam 22. A surface of each of the back and front joining portions 36, 38 may comprise a plurality of engaging elements. The engaging elements of the back joining portions 36 are adapted to repeatedly engage and disengage corresponding engaging elements of the front joining portions 38 to releasably secure absorbent article 10 in its three-dimensional wear configuration. The back and front joining portions 36, 38 may comprise any refastenable fasteners suitable for absorbent articles, such as adhesive fasteners, cohesive fasteners, mechanical fasteners, or the like. The back and front joining portions 36, 38 may comprise mechanical fastening components. Suitable mechanical fastening components may be provided by interlocking geometric shaped materials, such as hooks, loops, bulbs, mushrooms, arrowheads, balls on stems, male and female mating components, buckles, snaps, or the like. The back joining portions 36 (one on each side of the absorbent article 10) may comprise loop fasteners and the front joining portions 38 may comprise complementary hook fasteners. Alternatively, the back joining portions 36 may comprise hook fasteners and the front joining portions 38 may comprise complementary loop fasteners. The hooks fasteners may be integral with the back or front joining portions or may be manufactured from a portion of the back or front joining portions. Alternatively, the back and front joining portions 36, 38 may comprise interlocking similar surface fasteners, or adhesive and an adhesive-receptive landing zone or material, or hook fasteners and a nonwoven landing zone. When engaged, the back and front joining portions 36, 38 can define refastenable side seams 22.

The absorbent article 10 may further comprise one or more disposal fasteners 24, wherein the disposal fastener 24 is a disposal tab 26. In some aspects, the disposal tab 26 may be attached to each of the back ears 18 and extend in part transversely outward of the respective back ears for opposed relationship with the corresponding front ears in the wear configuration. In some aspects, the back ears 18 or front ears 20 may comprise a disposal tab extending beyond the back or front joining portions 36, 38. Each disposal tab 26 may comprise an attachment region 28 at which the disposal tab 26 is attached to the respective outer surface of the back or front ears 18, 20 of the absorbent article 10, and a fastener region 30 extending transversely outward from the attachment region 28. Alternatively, the disposal tab 26 may be integral with and form part of back ears 18 or front ears 20. The fastener region 30 of the disposal tab 26 may comprise a plurality of hook fasteners 32 that are integrally formed with a material of the disposal tab 26 for use in securing the absorbent article 10 in a compact disposal configuration. The disposal tab 26 may further comprise a grip region 34 transversely outward of the fastener region 30 for use in manually gripping and manipulating the disposal tab 26 relative to the absorbent article 10.

To dispose of the used absorbent article 10 after removal, the crotch region 14 and a portion of the back waist region 16 may be folded or rolled up over the front waist region 12. The disposal tabs 26 may then be gripped at grip regions 34 and pulled around the folded or rolled portion of the absorbent article 10 towards each other. The disposal tabs 26 may then engage a portion of the outer cover material, the back or front joining portions, or any other absorbent article component to secure the absorbent article in a compact configuration for disposal. This allows the absorbent article 10 to be relatively compact in the disposal configuration and to be held generally tightly in this configuration to reduce the risk of leakage of bodily exudates from the absorbent article.

Figure 28:
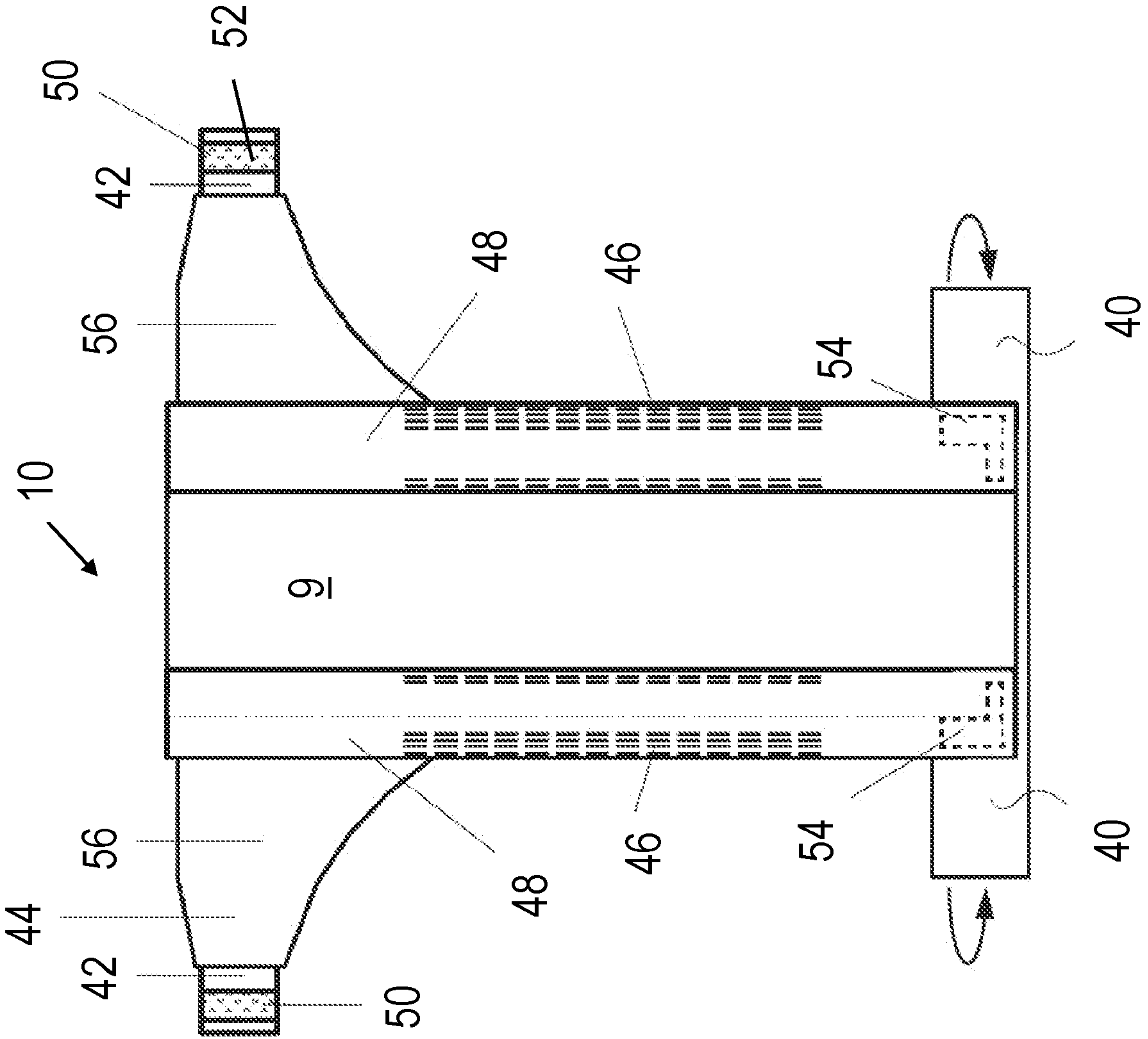
FIG. 28 is a schematic plan view of an example absorbent article in a flat, uncontracted state with a wearer-facing surface facing the viewer.

FIG. 28 is a schematic plan view of an example absorbent article in a flat, uncontracted state with the wearer-facing surface facing the viewer. The body-facing surface 9 of the absorbent article 10 is facing the viewer. In certain embodiments, the article 10 includes one or more lateral extension elements in the form of an ear, including for example front ears 40 disposed in a first waist region and/or back ears 42 disposed in a second waist region. Fastener attachment arms 42 may extend from the back ears 44. A leg gasketing system 48 may extend between the first waist region and the second waist region and may include elastic elements 46 to form one or more leg cuffs.

In various embodiments, the article 10 may also comprise a primary fastening system. A primary fastening system may comprise a fastening component 50, which may comprise one or more fastening elements 52 which cause the component to engage with another surface, such as a receiving component. In various embodiments, fastening elements comprise hooks. Receiving components may comprise material adapted to fastenably cooperate with fastening elements, such as a section or patch adapted to serve as cooperative loops material, to provide a hook-and-loop fastening system combination.

In various embodiments, the article 10 may also comprise a secondary fastening system. The secondary fastening system may comprise a secondary fastening component 54 and a secondary receiving component 56 that are operatively engageable to further secure the article about the wearer. The secondary fastening component 54 may be disposed in the first waist region, and the secondary fastening receiving component 56 may be disposed in the second waist region. Addition of a secondary fastening system can provide a greater surface area for fastening, and thereby de-concentrate lateral tensile forces communicated through the fastening location(s) as the rear waist region is pulled toward the front waist region, and vice versa, when the diaper is worn. In addition, having two distinct fastening locations reduces the tendency of the front portion of the article to pivot (i.e., pivot around the single fastening location of the primary fastening system). Further, the secondary system helps to create a line of tension closer to the front waist edge, which may reduce the likelihood of folding or flipping over of the front waist edge during wear. Further still, the secondary system may create an anchoring geodesic to direct forces from the crotch region to over the hips in order to prevent sagging during wearer. The secondary system may also help to secure the front ear or combination belt structures in place during wear. Each of the foregoing can serve to provide for more effective and durable fastening and less longitudinal and/or lateral flexing, sagging and/or wrinkling of the diaper materials about the fastening areas during wear.

Examples/Combinations

1. A laminate for an absorbent article comprising:
   - a first substrate comprising intermittent integrally formed protrusions and unformed areas between the intermittent integrally formed protrusions, wherein the protrusions are formed substantially from the first substrate, and wherein the first substrate has a first width; and
   - a second substrate joined to the first substrate, the second substrate having a second width, wherein the second width is greater than the first width; and
   - wherein the first substrate is joined to the second substrate in the unformed areas.

2. The laminate of Paragraph 1, wherein the first substrate comprises a film.

3. The laminate of Paragraph 1, wherein the first substrate comprises a bicomponent nonwoven.

4. The laminate of any one of the preceding paragraphs, wherein the protrusions are free from fibrous elements.

5. The laminate of any one of the preceding paragraphs, wherein the second substrate comprises a nonwoven.

6. The laminate of any one of the preceding paragraphs, wherein the first substrate has a higher basis weight than the second substrate.

7. The laminate of any one of the preceding paragraphs, wherein the first substrate comprises a plurality of discrete pieces, and wherein the second substrate is continuous.

8. An absorbent article comprising the laminate of any one of the preceding paragraphs.

9. The absorbent article of Paragraph 8, wherein the absorbent article is a taped diaper, and wherein the laminate forms a primary touch fastener.

10. The absorbent article of Paragraph 8, wherein the absorbent article is a taped diaper, and wherein the laminate forms a secondary touch fastener.

11. The absorbent article of Paragraph 8, wherein the absorbent article is a pant, and wherein the laminate forms a portion of a refastenable side seam.

12. The absorbent article of Paragraph 8, wherein the laminate forms a disposal tape.

13. A method of forming a laminate comprising:
   - providing a first device comprising an outer surface;
   - providing a second device comprising a first source of vibration energy;
   - forming a first nip between the first source of vibration energy and the outer surface;
   - conveying a first substrate through the first nip;
   - using the first source of vibration energy to alter a portion of a machine directional lane of the first substrate in the first nip to create an altered area;
   - providing a third device comprising a second source of vibration energy;
   - forming a second nip between the second source of vibration energy and the outer surface;
   - wherein the second nip is downstream of the first nip;
   - conveying the first substrate with the altered area and a second substrate into the second nip, wherein the first substrate has a first cross-directional width, wherein the second substrate has a second cross-directional width, and wherein the second cross-directional width is larger than the first cross-directional width; and
   - using the second source of vibration energy to join the first substrate to the second substrate in the second nip.

14. The method of Paragraph 13, wherein the altered area is intermittent in the machine directional lane.

15. The method of Paragraph 14, wherein the first substrate is joined to the second substrate intermediate the intermittent altered areas.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of forming a laminate comprising:

providing a first device comprising an outer surface;

providing a second device comprising a first source of vibration energy;

forming a first nip between the first source of vibration energy and the outer surface;

conveying a first substrate through the first nip;

using the first source of vibration energy to alter a portion of the first substrate in the first nip to create an altered area;

providing a third device comprising a second source of vibration energy;

forming a second nip between the second source of vibration energy and the outer surface;

wherein the second nip is downstream of the first nip;

conveying the first substrate with the altered area and a second substrate into the second nip; and using the second source of vibration energy to join the first substrate to the second substrate in the second nip.

2. The method of claim 1, wherein the second substrate is not conveyed through the first nip.

3. The method of claim 1, wherein the first substrate comprises a film.

4. The method of claim 1, wherein the first substrate comprises a bicomponent nonwoven.

5. The method of claim 1, wherein the second substrate is a nonwoven.

6. The method of claim 1, comprising intermittently altering the portion of the first substrate in the first nip to form intermittent altered areas.

7. The method of claim 1, comprising imparting thermal energy to the portion of the first substrate upstream of the first nip to heat the portion of the first substrate to a temperature below a melting temperature of the portion of the first substrate, wherein the temperature below the melting temperature of the portion of the first substrate is in a range of about 90 degrees C. to about 160 degrees C.

8. The method of claim 1, wherein the first substrate has a first width, wherein the second substrate has a second width, and wherein the first width is narrower than the second width.

9. The method of claim 1, wherein the first substrate comprises a first strip of material and a second strip of material, and wherein the second substrate has a width that is greater than a width of the first strip of material and a width the second strip of material combined.

10. The method of claim 1, wherein the first source of vibration energy or the second source of vibration energy is a rotary sonotrode.

11. The method of claim 1, wherein the first source of vibration energy or the second source of vibration energy is a blade sonotrode.

12. The method of claim 1, comprising heating the outer surface of the first device.

13. The method of claim 1, wherein the first substrate is joined to the second substrate in areas not comprising the altered area.

14. The method of claim 1, comprising cooling the first source of vibration energy, the second source of vibration energy, and/or the outer surface of the first device.

15. The method of claim 1, comprising providing a plurality of recesses in the outer surface of the first device, wherein the recesses have a shape configured to produce projections in the altered area suitable for use in a touch fastener.

16. The method of claim 1, wherein the altered area comprises hooks for a touch fastener.

17. The method of claim 1, comprising flatting areas of the first substrate upstream of the first nip.

18. A method of forming a laminate comprising:

providing a first device comprising an outer surface;

providing a second device comprising a first source of vibration energy;

forming a first nip between the first source of vibration energy and the outer surface;

conveying a first substrate through the first nip;

using the first source of vibration energy to alter a portion of a machine directional lane of the first substrate in the first nip to create an altered area;

providing a third device comprising a second source of vibration energy;

forming a second nip between the second source of vibration energy and the outer surface;

wherein the second nip is downstream of the first nip;

conveying the first substrate with the altered area and a second substrate into the second nip, wherein the first substrate has a first cross-directional width, wherein the second substrate has a second cross-directional width, and wherein the second cross-directional width is larger than the first cross-directional width; and using the second source of vibration energy to join the first substrate to the second substrate in the second nip.

19. The method of claim 18, wherein the altered area is intermittent in the machine directional lane.

20. The method of claim 19, wherein the first substrate is joined to the second substrate intermediate the intermittent altered areas.

* * * * *